United States Patent
Prakash et al.

(10) Patent No.: US 10,039,602 B2
(45) Date of Patent: *Aug. 7, 2018

(54) ELECTROSURGICAL ENERGY CHANNEL SPLITTERS AND SYSTEMS FOR DELIVERING ELECTROSURGICAL ENERGY

(71) Applicant: COVIDIEN LP, Mansfield, MA (US)

(72) Inventors: Mani Prakash, Boulder, CO (US); Francesca Rossetto, Longmont, CO (US); Steven Kim, Los Altos, CA (US); Brian Shiu, Sunnyvale, CA (US); Thomas J. Fogarty, Portola Valley, CA (US); Sascha Zarins, Los Gatos, CA (US)

(73) Assignee: Covidien LP, Mansfield, MA (US)

( * ) Notice: Subject to any disclaimer, the term of this patent is extended or adjusted under 35 U.S.C. 154(b) by 391 days.

This patent is subject to a terminal disclaimer.

(21) Appl. No.: 14/462,123

(22) Filed: Aug. 18, 2014

(65) Prior Publication Data

US 2014/0358139 A1    Dec. 4, 2014

Related U.S. Application Data

(60) Division of application No. 11/713,927, filed on Mar. 5, 2007, now Pat. No. 8,808,282, which is a
(Continued)

(51) Int. Cl.
*A61B 18/18* (2006.01)
*A61B 90/00* (2016.01)
(Continued)

(52) U.S. Cl.
CPC .......... *A61B 18/1815* (2013.01); *A61B 18/14* (2013.01); *A61B 18/18* (2013.01);
(Continued)

(58) Field of Classification Search
CPC . A61B 18/1815; A61B 18/18; A61B 18/1206; A61B 2018/183;
(Continued)

(56) References Cited

U.S. PATENT DOCUMENTS

| | | | |
|---|---|---|---|
| 2,022,065 A | 11/1935 | Wappler | |
| 2,047,535 A | 7/1936 | Wappler | |

(Continued)

FOREIGN PATENT DOCUMENTS

| | | | |
|---|---|---|---|
| AU | 0711612 B2 | 10/1999 | |
| CN | 1103807 A | 6/1995 | |

(Continued)

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.

(Continued)

*Primary Examiner* — Michael Peffley

(57) ABSTRACT

An electrosurgical energy channel splitter apparatus includes a channel input a plurality of channel outputs, and a controller. The channel input is configured to receive electrosurgical energy from an electrosurgical energy source. Each channel output is configured to couple to a respective electrosurgical device. The controller is coupled to the channel input and the plurality of channel outputs. The controller is configured to selectively direct the electrosurgical energy from the channel input to one of the plurality of channel outputs.

12 Claims, 37 Drawing Sheets

Related U.S. Application Data continuation of application No. 10/272,314, filed on Oct. 15, 2002, now Pat. No. 7,197,363.

(60) Provisional application No. 60/373,190, filed on Apr. 16, 2002.

(51) Int. Cl.
*A61B 18/14* (2006.01)
*A61B 19/00* (2006.01)
*A61B 18/00* (2006.01)

(52) U.S. Cl.
CPC .......... *A61B 90/39* (2016.02); *A61B 18/1477* (2013.01); *A61B 19/54* (2013.01); *A61B 2018/00577* (2013.01); *A61B 2018/00601* (2013.01); *A61B 2018/144* (2013.01); *A61B 2018/1425* (2013.01); *A61B 2018/1435* (2013.01); *A61B 2018/183* (2013.01); *A61B 2018/1823* (2013.01); *A61B 2018/1846* (2013.01); *A61B 2018/1861* (2013.01); *A61B 2019/5408* (2013.01); *A61B 2090/3908* (2016.02)

(58) Field of Classification Search
CPC .. A61B 2018/00577; A61B 2018/1823; A61B 2018/1876; A61B 2018/128
See application file for complete search history.

(56) References Cited

U.S. PATENT DOCUMENTS

| | | |
|---|---|---|
| 3,330,278 A | 7/1967 | Santomieri |
| 3,351,463 A | 11/1967 | Rozner |
| 3,516,412 A | 6/1970 | Ackerman |
| 3,598,108 A | 8/1971 | Jamshidi et al. |
| D223,367 S | 4/1972 | Kountz |
| 3,714,851 A | 2/1973 | Orser |
| 3,753,700 A | 8/1973 | Harrison et al. |
| 3,886,944 A | 6/1975 | Jamshidi |
| 3,890,977 A | 6/1975 | Wilson |
| 4,010,756 A | 3/1977 | DuMont et al. |
| 4,103,690 A | 8/1978 | Harris |
| 4,274,408 A | 6/1981 | Nimrod |
| 4,292,960 A | 10/1981 | Paglione |
| 4,311,154 A | 1/1982 | Sterzer et al. |
| D263,020 S | 2/1982 | Rau, III |
| 4,341,226 A | 7/1982 | Peters |
| D266,842 S | 11/1982 | Villers et al. |
| 4,402,328 A | 9/1983 | Doring |
| 4,448,198 A * | 5/1984 | Turner ................ A61N 5/02 607/62 |
| D278,306 S | 4/1985 | McIntosh |
| 4,557,272 A | 12/1985 | Carr |
| 4,565,200 A | 1/1986 | Cosman |
| 4,583,556 A | 4/1986 | Hines et al. |
| 4,592,356 A | 6/1986 | Gutierrez |
| 4,595,007 A | 6/1986 | Mericle |
| 4,612,940 A | 9/1986 | Kasevich et al. |
| 4,616,656 A | 10/1986 | Nicholson et al. |
| 4,621,642 A | 11/1986 | Chen |
| 4,633,880 A | 1/1987 | Osypka et al. |
| 4,658,836 A | 4/1987 | Turner |
| 4,665,906 A | 5/1987 | Jervis |
| 4,682,606 A | 7/1987 | DeCaprio |
| 4,700,716 A | 10/1987 | Kasevich et al. |
| D295,893 S | 5/1988 | Sharkany et al. |
| D295,894 S | 5/1988 | Sharkany et al. |
| 4,776,086 A | 10/1988 | Kasevich et al. |
| 4,799,495 A | 1/1989 | Hawkins et al. |
| 4,800,899 A | 1/1989 | Elliott |
| 4,825,880 A | 5/1989 | Stauffer et al. |
| 4,869,259 A | 9/1989 | Elkins |
| 4,925,445 A | 5/1990 | Sakamoto et al. |
| 4,966,583 A | 10/1990 | Debbas |
| 5,011,473 A | 4/1991 | Gatturna |
| 5,018,530 A | 5/1991 | Rank et al. |
| 5,059,197 A | 10/1991 | Urie et al. |
| 5,067,957 A | 11/1991 | Jervis |
| 5,085,659 A | 2/1992 | Rydell |
| 5,122,136 A | 6/1992 | Guglielmi et al. |
| 5,158,084 A | 10/1992 | Ghiatas |
| 5,171,255 A | 12/1992 | Rydell |
| 5,183,463 A | 2/1993 | Debbas |
| 5,190,054 A | 3/1993 | Fetter et al. |
| 5,190,546 A | 3/1993 | Jervis |
| 5,197,482 A | 3/1993 | Rank et al. |
| 5,205,829 A | 4/1993 | Lituchy |
| 5,217,027 A | 6/1993 | Hermens |
| 5,221,269 A | 6/1993 | Miller et al. |
| 5,246,438 A | 9/1993 | Langberg |
| 5,249,585 A | 10/1993 | Turner et al. |
| 5,282,845 A | 2/1994 | Bush et al. |
| 5,300,068 A | 4/1994 | Rosar et al. |
| 5,301,682 A | 4/1994 | Debbas |
| 5,314,466 A | 5/1994 | Stern et al. |
| 5,342,356 A * | 8/1994 | Ellman ................ A61B 18/14 606/32 |
| 5,344,441 A | 9/1994 | Gronauer |
| 5,350,419 A | 9/1994 | Bendel et al. |
| 5,353,804 A | 10/1994 | Kornberg et al. |
| 5,370,644 A | 12/1994 | Langberg |
| 5,370,675 A | 12/1994 | Edwards et al. |
| D354,218 S | 1/1995 | Van de Peer |
| 5,405,346 A | 4/1995 | Grundy et al. |
| 5,409,004 A | 4/1995 | Sloan |
| 5,462,062 A | 10/1995 | Rubinstein et al. |
| 5,470,308 A | 11/1995 | Edwards et al. |
| 5,472,441 A | 12/1995 | Edwards et al. |
| 5,486,183 A | 1/1996 | Middleman et al. |
| 5,488,958 A | 2/1996 | Topel et al. |
| 5,500,012 A | 3/1996 | Brucker et al. |
| 5,507,743 A | 4/1996 | Edwards et al. |
| 5,520,684 A | 5/1996 | Imran |
| 5,536,267 A * | 7/1996 | Edwards ................ C22F 1/183 604/22 |
| 5,540,683 A | 7/1996 | Ichikawa et al. |
| 5,556,377 A | 9/1996 | Rosen et al. |
| 5,556,410 A | 9/1996 | Mittermeir et al. |
| 5,558,673 A | 9/1996 | Edwards et al. |
| 5,578,030 A | 11/1996 | Levin |
| 5,599,294 A | 2/1997 | Edwards et al. |
| 5,599,295 A | 2/1997 | Rosen et al. |
| 5,599,346 A | 2/1997 | Edwards et al. |
| 5,607,389 A | 3/1997 | Edwards et al. |
| 5,672,173 A | 9/1997 | Gough et al. |
| 5,672,174 A | 9/1997 | Gough et al. |
| 5,683,384 A | 11/1997 | Gough et al. |
| 5,685,853 A | 11/1997 | Bonnet |
| 5,700,243 A | 12/1997 | Narciso, Jr. |
| 5,709,697 A | 1/1998 | Ratcliff et al. |
| 5,720,718 A | 2/1998 | Rosen et al. |
| 5,735,847 A | 4/1998 | Gough et al. |
| 5,741,225 A | 4/1998 | Lax et al. |
| 5,749,887 A | 5/1998 | Heske et al. |
| 5,776,176 A | 7/1998 | Rudie |
| 5,794,626 A | 8/1998 | Kieturakis |
| 5,795,308 A | 8/1998 | Russin |
| 5,800,484 A | 9/1998 | Gough et al. |
| 5,800,486 A | 9/1998 | Thome et al. |
| 5,807,339 A | 9/1998 | Bostrom et al. |
| 5,810,804 A | 9/1998 | Gough et al. |
| 5,853,366 A | 12/1998 | Dowlatshahi |
| 5,855,576 A | 1/1999 | LeVeen et al. |
| 5,861,002 A | 1/1999 | Desai |
| 5,863,290 A | 1/1999 | Gough et al. |
| 5,871,523 A | 2/1999 | Fleischman et al. |
| 5,879,357 A | 3/1999 | Heaton et al. |
| 5,882,316 A | 3/1999 | Chu et al. |
| 5,897,554 A | 4/1999 | Chia et al. |
| 5,902,310 A | 5/1999 | Foerster et al. |
| 5,904,690 A | 5/1999 | Middleman et al. |
| 5,904,691 A | 5/1999 | Barnett et al. |

(56) References Cited

U.S. PATENT DOCUMENTS

| | | | |
|---|---|---|---|
| 5,904,709 A | 5/1999 | Arndt et al. | |
| 5,928,229 A * | 7/1999 | Gough | A61B 18/1477 606/41 |
| 5,938,692 A | 8/1999 | Rudie | |
| 5,941,890 A | 8/1999 | Voegele et al. | |
| 5,954,655 A | 9/1999 | Hussman | |
| 5,954,719 A | 9/1999 | Chen et al. | |
| 5,957,969 A | 9/1999 | Warner et al. | |
| 5,974,343 A | 10/1999 | Brevard et al. | |
| 5,980,563 A | 11/1999 | Tu et al. | |
| 5,989,265 A | 11/1999 | Bouquet De La Joliniere et al. | |
| 6,007,495 A | 12/1999 | Matula | |
| 6,016,811 A | 1/2000 | Knopp et al. | |
| 6,019,757 A | 2/2000 | Scheldrup | |
| 6,022,362 A | 2/2000 | Lee et al. | |
| 6,026,331 A | 2/2000 | Feldberg et al. | |
| 6,027,501 A | 2/2000 | Goble et al. | |
| 6,027,524 A | 2/2000 | Petit | |
| 6,032,078 A | 2/2000 | Rudie | |
| 6,039,735 A | 3/2000 | Greep | |
| 6,050,954 A | 4/2000 | Mittermeier | |
| 6,051,008 A | 4/2000 | Saadat et al. | |
| 6,053,876 A | 4/2000 | Fisher | |
| 6,053,925 A | 4/2000 | Barnhart | |
| D424,693 S | 5/2000 | Pruter | |
| D424,694 S | 5/2000 | Tetzlaff et al. | |
| D425,201 S | 5/2000 | Tetzlaff et al. | |
| 6,056,744 A | 5/2000 | Edwards | |
| 6,059,780 A | 5/2000 | Gough et al. | |
| 6,068,627 A * | 5/2000 | Orszulak | A61B 18/12 606/34 |
| 6,071,280 A | 6/2000 | Edwards et al. | |
| 6,073,051 A | 6/2000 | Sharkey et al. | |
| 6,080,113 A | 6/2000 | Heneveld et al. | |
| 6,080,114 A | 6/2000 | Russin | |
| 6,080,150 A | 6/2000 | Gough | |
| 6,097,985 A | 8/2000 | Kasevich et al. | |
| 6,106,518 A | 8/2000 | Wittenberger et al. | |
| 6,106,524 A | 8/2000 | Eggers et al. | |
| 6,122,551 A | 9/2000 | Rudie et al. | |
| 6,134,476 A | 10/2000 | Arndt et al. | |
| 6,146,378 A | 11/2000 | Mikus et al. | |
| 6,146,379 A | 11/2000 | Fleischman et al. | |
| 6,146,657 A | 11/2000 | Unger et al. | |
| 6,162,216 A | 12/2000 | Guziak et al. | |
| 6,176,856 B1 | 1/2001 | Jandak et al. | |
| 6,178,354 B1 | 1/2001 | Gibson | |
| 6,181,970 B1 | 1/2001 | Kasevich | |
| 6,217,528 B1 | 4/2001 | Koblish et al. | |
| 6,223,086 B1 | 4/2001 | Carl et al. | |
| 6,233,490 B1 | 5/2001 | Kasevich | |
| 6,245,064 B1 | 6/2001 | Lesh et al. | |
| 6,245,318 B1 | 6/2001 | Klibanov et al. | |
| 6,251,128 B1 | 6/2001 | Knopp et al. | |
| 6,275,738 B1 | 8/2001 | Kasevich et al. | |
| 6,277,113 B1 | 8/2001 | Berube | |
| 6,287,304 B1 | 9/2001 | Eggers et al. | |
| 6,290,715 B1 | 9/2001 | Sharkey et al. | |
| D449,886 S | 10/2001 | Tetzlaff et al. | |
| 6,306,132 B1 | 10/2001 | Moorman et al. | |
| 6,308,091 B1 | 10/2001 | Avitall | |
| 6,325,796 B1 | 12/2001 | Berube et al. | |
| 6,330,479 B1 | 12/2001 | Stauffer | |
| 6,346,104 B2 | 2/2002 | Daly et al. | |
| 6,347,251 B1 * | 2/2002 | Deng | A61B 18/1477 606/41 |
| 6,355,033 B1 | 3/2002 | Moorman et al. | |
| D457,958 S | 5/2002 | Dycus et al. | |
| D457,959 S | 5/2002 | Tetzlaff et al. | |
| 6,405,733 B1 | 6/2002 | Fogarty et al. | |
| 6,461,351 B1 | 10/2002 | Woodruff et al. | |
| 6,471,696 B1 | 10/2002 | Berube et al. | |
| 6,496,738 B2 | 12/2002 | Carr | |
| 6,514,251 B1 | 2/2003 | Ni et al. | |
| 6,530,922 B2 | 3/2003 | Cosman et al. | |
| 6,564,806 B1 | 5/2003 | Fogarty et al. | |
| 6,569,159 B1 | 5/2003 | Edwards et al. | |
| 6,582,426 B2 | 6/2003 | Moorman et al. | |
| 6,622,731 B2 | 9/2003 | Daniel et al. | |
| 6,623,423 B2 * | 9/2003 | Sakurai | A61B 17/320068 600/104 |
| 6,652,520 B2 | 11/2003 | Moorman et al. | |
| 6,663,624 B2 | 12/2003 | Edwards et al. | |
| 6,679,875 B2 * | 1/2004 | Honda | A61B 17/00 606/1 |
| D487,039 S | 2/2004 | Webster et al. | |
| 6,685,700 B2 | 2/2004 | Behl et al. | |
| 6,692,494 B1 | 2/2004 | Cooper et al. | |
| 6,699,241 B2 | 3/2004 | Rappaport et al. | |
| 6,722,371 B1 | 4/2004 | Fogarty et al. | |
| 6,752,154 B2 | 6/2004 | Fogarty et al. | |
| 6,752,767 B2 | 6/2004 | Turovskiy et al. | |
| D496,997 S | 10/2004 | Dycus et al. | |
| D499,181 S | 11/2004 | Dycus et al. | |
| 6,878,147 B2 | 4/2005 | Prakash et al. | |
| 6,936,047 B2 | 8/2005 | Nasab et al. | |
| 6,958,062 B1 | 10/2005 | Gough et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| 7,160,292 B2 | 1/2007 | Moorman et al. | |
| 7,160,296 B2 | 1/2007 | Pearson et al. | |
| 7,195,630 B2 | 3/2007 | Ciarrocca | |
| D541,418 S | 4/2007 | Schechter et al. | |
| D541,938 S | 5/2007 | Kerr et al. | |
| 7,220,259 B2 | 5/2007 | Harrington et al. | |
| 7,226,446 B1 | 6/2007 | Mody et al. | |
| 7,228,164 B2 | 6/2007 | Fuimaono et al. | |
| 7,229,438 B2 | 6/2007 | Young | |
| 7,257,435 B2 | 8/2007 | Plaza | |
| 7,258,690 B2 | 8/2007 | Sutton et al. | |
| 7,261,711 B2 | 8/2007 | Mulier et al. | |
| 7,261,712 B2 | 8/2007 | Burbank et al. | |
| 7,267,683 B2 | 9/2007 | Sharkey et al. | |
| 7,276,064 B2 | 10/2007 | Paul et al. | |
| 7,282,049 B2 * | 10/2007 | Orszulak | A61B 18/1206 606/34 |
| 7,282,051 B2 | 10/2007 | Rioux et al. | |
| 7,282,061 B2 | 10/2007 | Sharkey et al. | |
| 7,285,119 B2 | 10/2007 | Stewart et al. | |
| 7,294,125 B2 | 11/2007 | Phalen et al. | |
| 7,306,591 B2 | 12/2007 | Thomas et al. | |
| 7,306,595 B2 | 12/2007 | Ostrovsky et al. | |
| 7,322,938 B2 | 1/2008 | Burbank et al. | |
| 7,322,939 B2 | 1/2008 | Burbank et al. | |
| 7,322,940 B2 | 1/2008 | Burbank et al. | |
| 7,326,201 B2 | 2/2008 | Fjield et al. | |
| 7,326,208 B2 | 2/2008 | Vanney et al. | |
| 7,329,253 B2 | 2/2008 | Brounstein et al. | |
| 7,331,959 B2 | 2/2008 | Cao et al. | |
| 7,331,960 B2 | 2/2008 | Schaer | |
| 7,335,196 B2 | 2/2008 | Swanson et al. | |
| 7,335,197 B2 | 2/2008 | Sage et al. | |
| 7,335,198 B2 | 2/2008 | Eggers et al. | |
| D564,662 S | 3/2008 | Moses et al. | |
| D576,932 S | 9/2008 | Strehler | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| D634,010 S | 3/2011 | DeCarlo | |
| D681,810 S | 5/2013 | Decarlo | |
| 8,808,282 B2 | 8/2014 | Prakash et al. | |
| 2001/0001819 A1 | 5/2001 | Lee et al. | |
| 2001/0037812 A1 | 11/2001 | Dobak et al. | |
| 2001/0051131 A1 | 12/2001 | Unger | |
| 2002/0022832 A1 | 2/2002 | Mikus et al. | |
| 2002/0059938 A1 | 5/2002 | Fogarty et al. | |
| 2002/0072742 A1 * | 6/2002 | Schaefer | A61B 18/1477 606/41 |
| 2002/0087151 A1 | 7/2002 | Mody et al. | |
| 2002/0133148 A1 | 9/2002 | Daniel et al. | |
| 2002/0147444 A1 | 10/2002 | Shah et al. | |

(56) References Cited

U.S. PATENT DOCUMENTS

| | | |
|---|---|---|
| 2002/0198520 A1 | 12/2002 | Coen et al. |
| 2003/0004506 A1 | 1/2003 | Messing |
| 2003/0065317 A1 | 4/2003 | Rudie et al. |
| 2003/0069578 A1 | 4/2003 | Hall et al. |
| 2003/0088242 A1 | 5/2003 | Prakash et al. |
| 2003/0109862 A1 | 6/2003 | Prakash et al. |
| 2003/0195499 A1 | 10/2003 | Prakash et al. |
| 2003/0195500 A1 | 10/2003 | Moorman et al. |
| 2003/0208199 A1 | 11/2003 | Keane |
| 2004/0168692 A1 | 9/2004 | Fogarty et al. |
| 2004/0225286 A1 | 11/2004 | Elliott |
| 2004/0267156 A1 | 12/2004 | Turovskiy et al. |
| 2005/0062666 A1 | 3/2005 | Prakash et al. |
| 2005/0070895 A1 | 3/2005 | Ryan et al. |
| 2005/0085881 A1 | 4/2005 | Prakash et al. |
| 2006/0217702 A1 | 9/2006 | Young |
| 2007/0049921 A1 | 3/2007 | Konishi et al. |
| 2007/0100405 A1 | 5/2007 | Thompson et al. |
| 2007/0118110 A1 | 5/2007 | Girard et al. |
| 2007/0129710 A1 | 6/2007 | Rudko et al. |
| 2007/0129721 A1 | 6/2007 | Phan et al. |
| 2007/0135700 A1 | 6/2007 | Taimisto et al. |
| 2007/0149963 A1 | 6/2007 | Matsukuma et al. |
| 2007/0149966 A1 | 6/2007 | Dahla et al. |
| 2007/0161977 A1 | 7/2007 | Moorman et al. |
| 2007/0179491 A1 | 8/2007 | Kratoska et al. |
| 2007/0179494 A1 | 8/2007 | Faure |
| 2007/0179496 A1 | 8/2007 | Swoyer et al. |
| 2007/0185483 A1 | 8/2007 | Butty et al. |
| 2007/0198006 A1 | 8/2007 | Prakash et al. |
| 2007/0203480 A1 | 8/2007 | Mody et al. |
| 2007/0203486 A1 | 8/2007 | Young |
| 2007/0219546 A1 | 9/2007 | Mody et al. |
| 2007/0232871 A1 | 10/2007 | Sinofsky et al. |
| 2007/0260234 A1 | 11/2007 | McCullagh et al. |
| 2007/0265609 A1 | 11/2007 | Thapliyal et al. |
| 2007/0265610 A1 | 11/2007 | Thapliyal et al. |
| 2007/0270789 A1 | 11/2007 | Berger |
| 2007/0270794 A1 | 11/2007 | Anderson et al. |
| 2007/0287996 A1 | 12/2007 | Rioux |
| 2007/0287999 A1 | 12/2007 | Malecki et al. |
| 2007/0293856 A1 | 12/2007 | Paul et al. |
| 2007/0299434 A1 | 12/2007 | Malecki et al. |
| 2007/0299435 A1 | 12/2007 | Crowe et al. |
| 2008/0004615 A1 | 1/2008 | Woloszko et al. |

FOREIGN PATENT DOCUMENTS

| | | |
|---|---|---|
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10217281 A1 | 10/2003 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0385604 A2 | 9/1990 |
| EP | 0395997 A1 | 11/1990 |
| EP | 0 481 685 A1 | 4/1992 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 667 126 A1 | 8/1995 |
| EP | 0829232 A2 | 3/1998 |
| EP | 0 836 868 A2 | 4/1998 |
| EP | 0 882 955 A1 | 12/1998 |
| EP | 00908154 A1 | 4/1999 |
| EP | 0908156 A1 | 4/1999 |
| EP | 1 159 926 A2 | 12/2001 |
| EP | 1559377 A1 | 8/2005 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 56-161636 | 12/1981 |
| JP | 59-58933 | 4/1984 |
| JP | 5-5106 | 1/1993 |
| JP | 5-08933 | 2/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 9117456 | 5/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2002253569 A | 9/2002 |
| JP | 2008142467 A | 6/2008 |
| KR | 20070093068 A | 9/2007 |
| KR | 20100014406 A | 2/2010 |
| KR | 20120055063 A | 5/2012 |
| SU | 166452 | 11/1964 |
| SU | 401367 A1 | 10/1973 |
| SU | 727201 A2 | 4/1980 |
| WO | 8806864 A1 | 9/1988 |
| WO | 9212678 A1 | 8/1992 |
| WO | 93/20767 A1 | 10/1993 |
| WO | 93/20768 A1 | 10/1993 |
| WO | 9627328 A1 | 9/1996 |

(56) References Cited

FOREIGN PATENT DOCUMENTS

| | | |
|---|---|---|
| WO | 96/34571 A1 | 11/1996 |
| WO | 97/40760 A1 | 11/1997 |
| WO | 97/48449 A1 | 12/1997 |
| WO | 97/48450 A1 | 12/1997 |
| WO | 97/48451 A1 | 12/1997 |
| WO | 9806341 A1 | 2/1998 |
| WO | 9830160 A1 | 7/1998 |
| WO | 9902095 A1 | 1/1999 |
| WO | 9904704 A2 | 2/1999 |
| WO | 9925248 A1 | 5/1999 |
| WO | 9943268 A1 | 9/1999 |
| WO | 9944506 A1 | 9/1999 |
| WO | 99/56642 A1 | 11/1999 |
| WO | 99/56643 A1 | 11/1999 |
| WO | 99/56812 A2 | 11/1999 |
| WO | 9958065 A1 | 11/1999 |
| WO | 9966834 A1 | 12/1999 |
| WO | 0010471 A1 | 3/2000 |
| WO | 0012009 A2 | 3/2000 |
| WO | 0012010 A1 | 3/2000 |
| WO | 0013602 A2 | 3/2000 |
| WO | 0016697 A2 | 3/2000 |
| WO | 0024320 A1 | 5/2000 |
| WO | 0028913 A1 | 5/2000 |
| WO | 00/36985 A2 | 6/2000 |
| WO | 0030531 A1 | 6/2000 |
| WO | 0033743 A1 | 6/2000 |
| WO | 00/49957 A1 | 8/2000 |
| WO | 00/51513 A1 | 9/2000 |
| WO | 0056239 A1 | 9/2000 |
| WO | 0057811 A1 | 10/2000 |
| WO | 0100114 A1 | 1/2001 |
| WO | 0105317 A1 | 1/2001 |
| WO | 0105320 A1 | 1/2001 |
| WO | 01/60235 A2 | 8/2001 |
| WO | 03/034932 A1 | 5/2003 |
| WO | 03/039385 A2 | 5/2003 |
| WO | 03/088806 A2 | 10/2003 |
| WO | 03/088858 A1 | 10/2003 |
| WO | 2005/011049 A2 | 2/2005 |
| WO | 2010/035831 A1 | 4/2010 |

OTHER PUBLICATIONS

Anderson et al., "A Numerical Study of Rapid Heating for High Temperature Radio Frequency Hyperthermia" International Journal of Bio-Medical Computing, 35 (1994), pp. 297-307.
Anonymous. Blunt Tubes with Finished Ends. Pointed Cannula, Popper & Sons Biomedical Instrument Division, (Products Price List), one page, Jul. 19, 2000
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chung et al., "Clinical Experience of Sutureless Closed Hemorrhoidectomy with LigaSureTM" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic LA Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSureTM Vessel Sealing System in Bloodless Hemorrhoidectomy" Innovations That Work, Mar. 2000.

(56) References Cited

OTHER PUBLICATIONS

Joseph Ortenberg, "LigaSureTM System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Koyle et al., "Laparoscopic Palomo Varicocele Ligation in Children and Adolescents" Pediatric Endosurgery & Innovative Techniques, vol. 6, No. 1, 2002.
LigaSureTM Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Ni Wei et al., "A Signal Processing Method for the Coriolis Mass Flowmeter Based on a Normalized . . . " Journal of Applied Sciences-Yingyong Kexue Xuebao, Shangha CN, vol. 23, No. 2:(Mar. 2005); pp. 160-184.
European Examination Report from Application No. EP 03 736 458.5 dated Jul. 17, 2015.
International Search Report EP10185413 dated Mar. 14, 2011.
International Search Report EP10185413 dated Dec. 7, 2010.
International Search Report for International Application No. EP 07 01 8821 dated Jan. 14, 2008.
Anonymous. (1987). Homer Mammalok .RTM. Breast Lesion Needle/Wire Localizer, Namic .RTM. Angiographic Systems Division, Glens Falls, New York, (Hospital products price list), 4 pages.
Anonymous. (1999). Auto Suture MIBB Site Marker: Single Use Clip Applier, United States Surgical (Product instructions), 2 pages.
Anonymous. (1999). MIBB Site Marker, United States Surgical (Sales brochure), 4 pages.
Anonymous. (2001). Disposable Chiba Biopsy Needles and Trays, Biopsy and Special Purpose Needles Cook Diagnostic and Interventional Products Catalog (Products list), 4 pages.
Chou, C.K. (1995). "Radiofrequency Hyperthermia in Cancer Therapy," Chapter 94 in Biologic Effects of Nonionizing Electromagnetic Fields. CRC Press, Inc. pp. 1424-1428.
Gennari, R. et al. (Jun. 2000). "Use of Technetium-99m-Labeled Colloid Albumin for Preoperative and Intraoperative Localization of Nonpalpable Breast Lesions," J. Am. Coll. Surg. 190(6):692-699.
Kopans, D.B. et al. (Nov. 1985). "Spring Hookwire Breast Lesion Localizer: Use with Rigid-Compression. Mammographic Systems," Radiology 157(2):537-538.
MDTECH product literature. (Mar. 2000). "D Wire": product description, one page.
MDTECH product literature. (Dec. 1999). "FlexStrand": product description, one page.
Mullan, B.F. et al. (May 1999). "Lung Nodules: Improved Wire for CT-Guided Localization," Radiology 211:561-565.
Urologix, Inc.—Medical Professionals: Targis.TM. Technology (Date Unknown). "Overcoming the Challenge" located at: <http://www.urologix.com/medical/technology.html> last visited on Apr. 27, 2001. Three pages.
Urrutia et al. (1988). "Retractable-Barb Needle for Breast Lesion Localization: Use in 60 Cases," Radiology 169 (3):845-847.
Joseph G. Andriole, M.D., et al., "Biopsy Needle Characteristics Assessed in the Laboratory", Radiology 148: 659-662, Sep. 1983.
T. Matsukawa, et al. "Percutaneous Microwave Coagulation Therapy in Liver Tumors", Acta Radiologica vol. 38, pp. 410-415, 1997.
C.F. Gottlieb, et al. "Interstitial Microwave Hyperthermia Applicators having Submillimetre Diameters", Int. J. Hyperthermia, vol. 6, No. 3, pp. 707-714, 1990.
Sylvain Labonte, et al., "Monopole Antennas for Microwave Catheter Ablation", IEEE Trans. on Microwave Theory and Techniques, vol. 44, No. 10, pp. 1832-1840, Oct. 1995.
Magdy F. Iskander, et al., "Design Optimization of Interstitial Antennas", IEEE Transactions on Biomedical Engineering, vol. 36, No. 2, Feb. 1989, pp. 238-246.
C.H. Durney, et al., "Antennas for Medical Applications", Antenna Handbook: Theory Application and Design, p. 24-40, Van Nostrand Reinhold, 1988 New York, V.T. Lo, S.W. Lee.
Murakami, R. et al., (1995). "Treatment of Hepatocellular Carcinoma: Value of Percutaneous Microwave Coagulation," American Journal of Radiology (AJR) 164:1159-1164.
Seki, T. et al., (1994). "Ultrasonically Guided Percutaneous Microwave Coagulation Therapy for Small Hepatocellular Carcinoma," Cancer 74(3): 817-825.
International Search Report for patent application No. EP 03 72 1482 dated Feb. 6, 2006.
International Search Report for International Application No. PCT/US03/09483 dated Aug. 13, 2003.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochennnotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.

(56) References Cited

OTHER PUBLICATIONS

Solbiati et al., (2001) "Percutaneous Radio-frequency Ablation of Hepatic Metastases from Colorectal Cancer: Longterm Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Stagegaard, N., Petersen H.H., Chen X., Svendsen J.H., "Indication of the Radiofrequency Induced Lesion Size by Pre-ablation Measurements" Europace (2005) 7, 525-534.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098; dated Oct. 14, 1993; Roger A. Stern.
U.S. Appl. No. 08/483,742; dated Jun. 7, 1995; Roger A. Stern.
U.S. Appl. No. 14/011,414; filed Aug. 27, 2013; inventor: Ohri.
U.S. Appl. No. 14/011,438; filed Aug. 27, 2013; inventor: Ohri.
U.S. Appl. No. 14/242,019; filed Apr. 1, 2014; inventor: Brannan.
U.S. Appl. No. 14/242,048; filed Apr. 1, 2014; inventor: Prakash.
U.S. Appl. No. 14/281,264; filed May 19, 2014; inventor: Prakash.
U.S. Appl. No. 14/281,344; filed May 19, 2014; inventor: Shiu.
U.S. Appl. No. 14/300,824; filed Jun. 10, 2014; inventor: Behnke.
U.S. Appl. No. 14/300,871; filed Jun. 10, 2014; inventor: Bonn.
U.S. Appl. No. 14/306,865; filed Jun. 17, 2014; inventor: Brannan.

\* cited by examiner

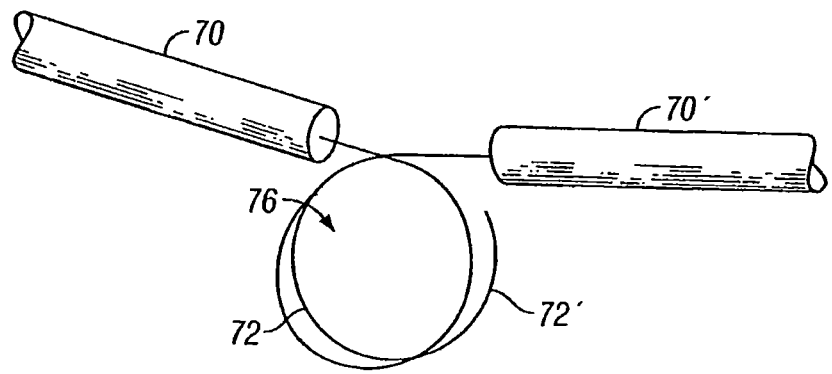
FIG. 4
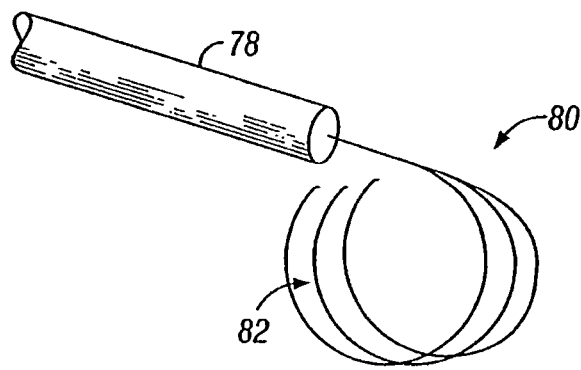 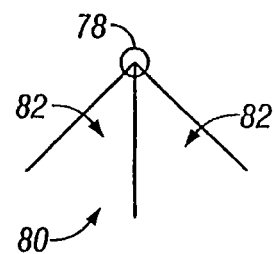
FIG. 5A  FIG. 5B

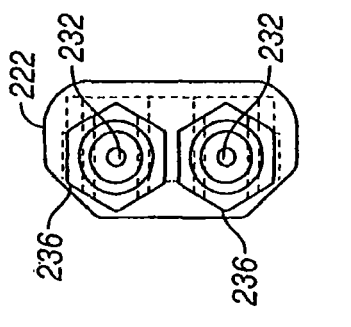
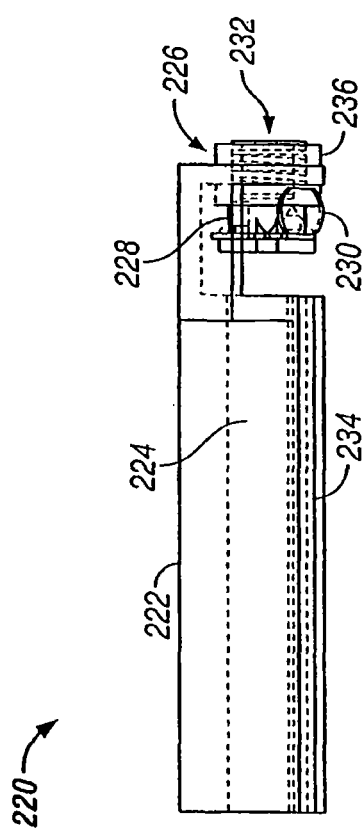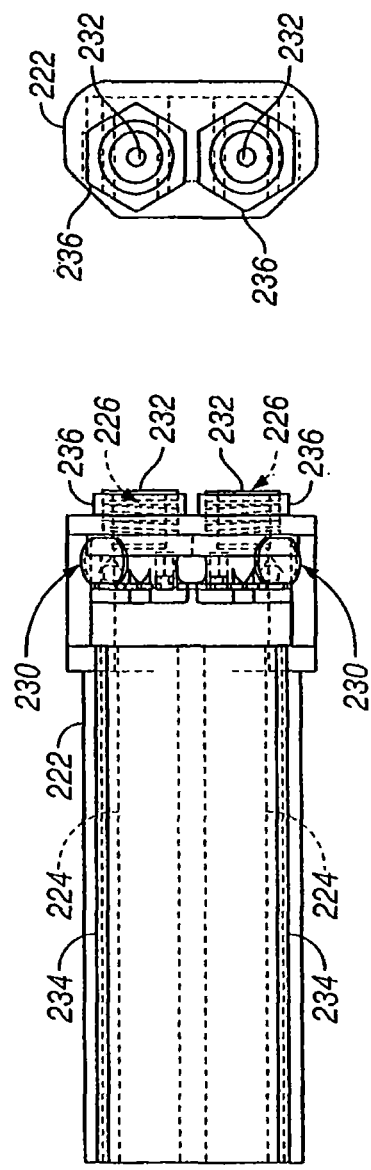

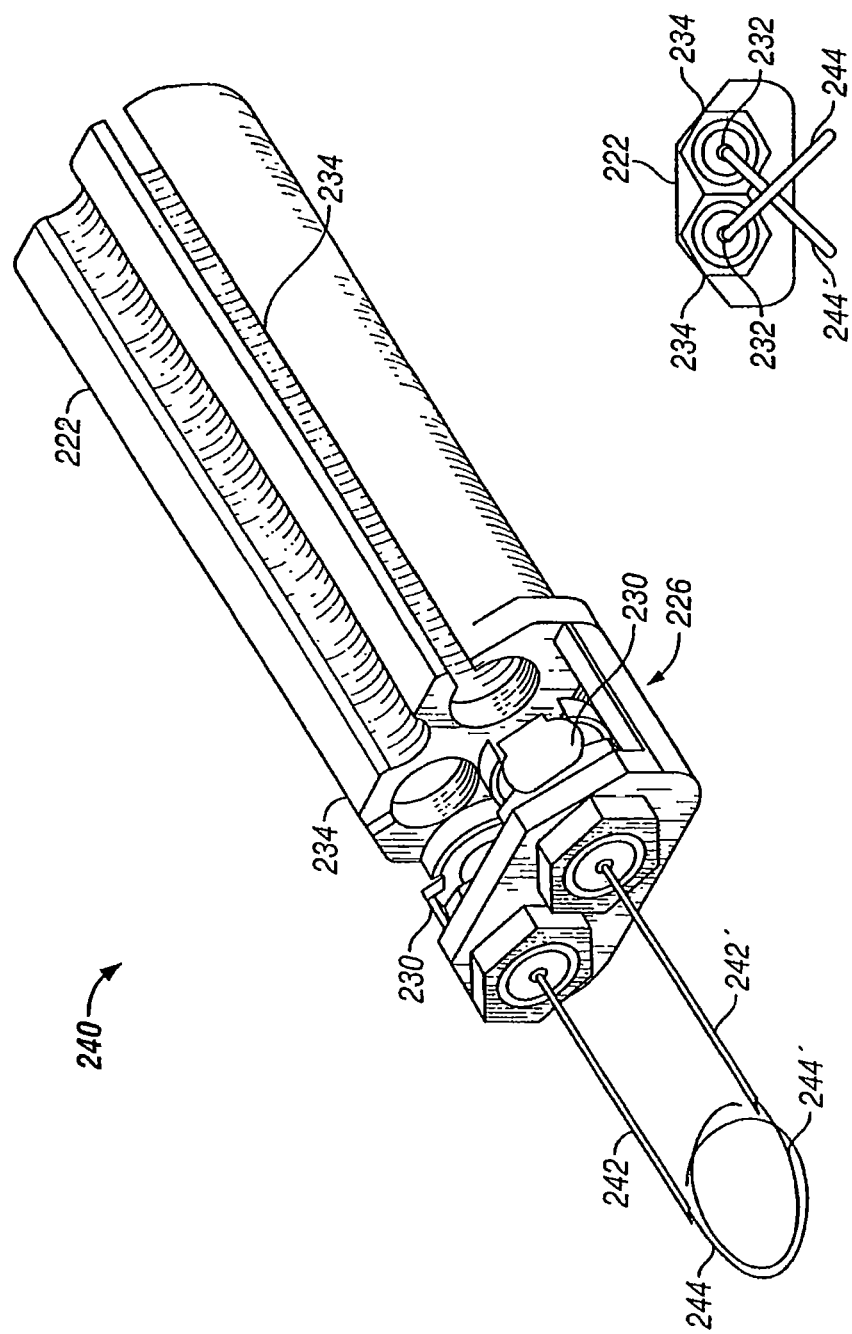

ELECTROSURGICAL ENERGY CHANNEL SPLITTERS AND SYSTEMS FOR DELIVERING ELECTROSURGICAL ENERGY

CROSS-REFERENCE TO RELATED APPLICATIONS

This application is a Divisional Application of U.S. application Ser. No. 11/713,927 now U.S. Pat. No. 8,808,282), filed on Mar. 5, 2007, which is a Continuation Application of U.S. application Ser. No. 10/272,314 (now U.S. Pat. No. 7,197,363), filed on Oct. 15, 2002, which claims the benefit of and priority to U.S. Provisional Application Ser. No. 60/373,190, filed on Apr. 16, 2002, the entire contents of each of which is incorporated by reference herein.

BACKGROUND

Technical Field

The invention relates generally to microwave antenna probes which may be used in tissue ablation applications. More particularly, the invention relates to microwave antennas which have curved configurations for insertion into tissue.

Background of Related Art

In the treatment of diseases such as cancer, certain types of cancer cells have been found to denature at elevated temperatures which are slightly lower than temperatures normally injurious to healthy cells. These types of treatments, known generally as hyperthermia therapy, typically utilize electromagnetic radiation to heat diseased cells to temperatures above 41° C. while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill it. Many procedures and types of devices utilizing electromagnetic radiation therapy are known in the art. Such microwave therapy is typically used in the treatment of tissue and organs such as the prostate, heart, and liver.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control. This is partly why a more direct and precise method of applying microwave radiation has been sought.

Presently, there are several types of microwave probes in use, e.g., monopole, dipole, and helical. One type is a monopole antenna probe, which consists of a single, elongated microwave conductor exposed at the end of the probe. The probe is sometimes surrounded by a dielectric sleeve. The second type of microwave probe commonly used is a dipole antenna, which consists of a coaxial construction having an inner conductor and an outer conductor with a dielectric separating a portion of the inner conductor and a portion of the outer conductor. In the monopole and dipole antenna probe, microwave energy generally radiates perpendicularly from the axis of the conductor.

Because of the perpendicular pattern of microwave energy radiation, conventional antenna probes are typically designed to be inserted directly into the tissue, e.g., a tumor, to be radiated. However, such typical antenna probes commonly fail to provide uniform heating axially and/or radially about the effective length of the probe.

It is especially difficult to assess the extent to which the microwave energy will radiate into the surrounding tissue, i.e., it is difficult to determine the area or volume of surrounding tissue which will be ablated. Furthermore, when conventional microwave antennas are inserted directly into the tissue, e.g., cancerous tissue, there is a danger of dragging or pulling cancerous cells along the antenna body into other parts of the body during insertion, placement, or removal of the antenna probe.

One conventional method for inserting and/or localizing wires or guides is described in U.S. Pat. No. 5,221,269 entitled "Guide for Localizing a Nonpalpable Breast Lesion" to Miller et al. which is incorporated herein by reference in its entirety. Miller describes a wire guide which is delivered into breast tissue through a tubular introducer needle. When deployed, the wire guide cuts into and scribes a helical path about the tissue distal to a lesion while the remainder of the distal portion of the wire guide follows the path scribed by the distal tip and locks about the tissue. However, Miller does not teach any structures for curved microwave antennas or their methods of use for surrounding predetermined regions of tissue for treatment.

U.S. Pat. No. 5,507,743 entitled "Coiled RF Electrode Treatment Apparatus" to Edwards et al., which is incorporated herein by reference in its entirety, describes an RF treatment apparatus for hyperthermia at low temperature which is also able to effect microwave treatment via an RF indifferent electrode which forms a helical structure. However, the electrode, which is deployed from an introducing catheter, comprises a hollow tubular structure with fluid ports defined along the structure.

Accordingly, there remains a need for a microwave antenna which overcomes the problems discussed above. There also exists a need for a microwave antenna which can be inserted into tissue and which produces a clearly defined area or volume of ablation. Moreover, there is also a need for a microwave antenna which can ablate an area or volume of tissue without ever having to directly contact the ablated tissue.

SUMMARY

A microwave ablation device is described below which is able to clearly define an ablation region by having the antenna surround at least a majority of the tissue to be ablated without the need to actually penetrate or contact the targeted region of tissue. This is accomplished in part by a microwave antenna probe which has a curved antenna portion ranging in size anywhere from several millimeters to several centimeters depending upon the size of the tissue to be treated. Various conductive materials may be used to fabricate the antenna, such as stainless steel or Nitinol. Moreover, a dielectric coating may be placed over at least a majority of curved antenna to aid with the insertion of the antenna into the tissue as well as to aid in preventing the tissue from sticking to the antenna.

The curved antenna portion is preferably curved to form a loop or enclosure which is selectively formed large enough for surrounding a region of tissue. When microwave energy is delivered through the feedline, any part of the feedline or antenna that completes the enclosure becomes part of the radiating portion. Rather than radiating directly along the length of the antenna, as one skilled in the art would normally expect, the curved configuration forms an ablation field or region defined by the curved antenna and any tissue enclosed within the ablation region becomes irradiated by the microwave energy. Thus, the curved antenna also serves as a boundary which is able to clearly define what tissue will be irradiated, thereby reducing the amount of undesirable damage to healthy surrounding tissue. Furthermore, the curved antenna also defines a predictable region of tissue outside the irradiated zone which will also be irradiated. This margin of tissue is generally very predictable and serves to treat the tissue a short distance outside the ablation region to ensure complete treatment of the area.

The curved antenna may be formed into a variety of shapes so long as the antenna preferably forms a substantially enclosed loop or enclosure, i.e., the curved antenna surrounds at least a majority of the tissue to be enclosed. Accordingly, the antenna may be formed into shapes such as circles, ellipses, spirals, helixes, squares, rectangles, triangles, etc., various other polygonal or smooth shapes, and partial forms of the various shapes so long as a majority of the enclosed tissue is surrounded. The curved antenna may be looped or wound about the selected tissue region anywhere from about 180° to 360° or greater, relative to a central point defined by the curved antenna. The curved antenna is preferably wound at an angle greater than 180°.

Multiple curved antennas may be used in conjunction with one another by positioning separate antennas adjacently or at different angles depending upon the size and shape of the tissue to be treated. Moreover, other variations on the curved antenna may have a single antenna body or feedline with multiple curved antennas extending therefrom.

To facilitate desirable placement and positioning of multiple antennas within the tissue to be treated, various alignment assembly devices may be utilized. Such alignment devices may be used to align and securely position the antennas to form various ablation region depending upon the desired results. Furthermore, the various alignment devices may be used to align and position a single antenna or a plurality of antennas deployed during a procedure.

Deployment and positioning of the microwave antennas may also be achieved through one of several different methods. For instance, antennas may be positioned within the tissue using introducers and wires for guiding placement of the antennas. Alternatively, other methods may involve using RF energy to facilitate deployment within the tissue. The microwave antenna is preferably insulated along most of its length, but the distal tip may be uninsulated such that the RF energy may be applied thereto to provide a cutting mechanism through the tissue. The generator used to supply the RF energy may be a separate unit or it may be integrated with the microwave energy generator within a single unit.

Moreover, another variation which may be utilized involves creating multiple channels from a single unit by multiplexing and cycling the output. This is particularly useful when using multiple microwave antennas. A channel splitter assembly may be used to create multiple channels by using a single source. Any number of multiple outputs may be used depending upon the desired number of channels and the desired effects. Additionally, the rate of cycling may range anywhere from several microseconds to several seconds over a treatment period of several minutes or longer.

Additional features may also be employed, e.g., to enhance the safety of the microwave antennas. For instance, a connection mechanism may allow for antenna connection with an outer shell of a conventional or custom connector. Such a feature may be configured to allow an electrical connection upon full deployment of the inner conductor of the curved antenna and no electrical connection during antenna deployment.

Furthermore, the curved shape of the antenna may allow for various applications within the body aside from tumor ablation. For instance, the curved antenna may be used to treat or seal, e.g., aneurysms, malfunctioning vessels, fistulas, bone metastases, etc., among other conditions or regions of the body.

BRIEF DESCRIPTION OF THE DRAWINGS

FIG. 4 shows another variation for using multiple curved antennas in which the antennas approach the region of tissue from different locations and angles.

FIGS. 5A and 5B show isometric and end views, respectively, of an antenna having a single feedline with multiple antenna loops extending therefrom.

FIGS. 9A to 9C show side, top, and end views, respectively, of another variation of antenna guide assembly which may be used to align microwave antennas.

FIGS. 11A and 11B show isometric and end views, respectively, of the antenna guide assembly of FIGS. 9A to 9C having microwave antennas positioned within.

DETAILED DESCRIPTION

Figure 1A:
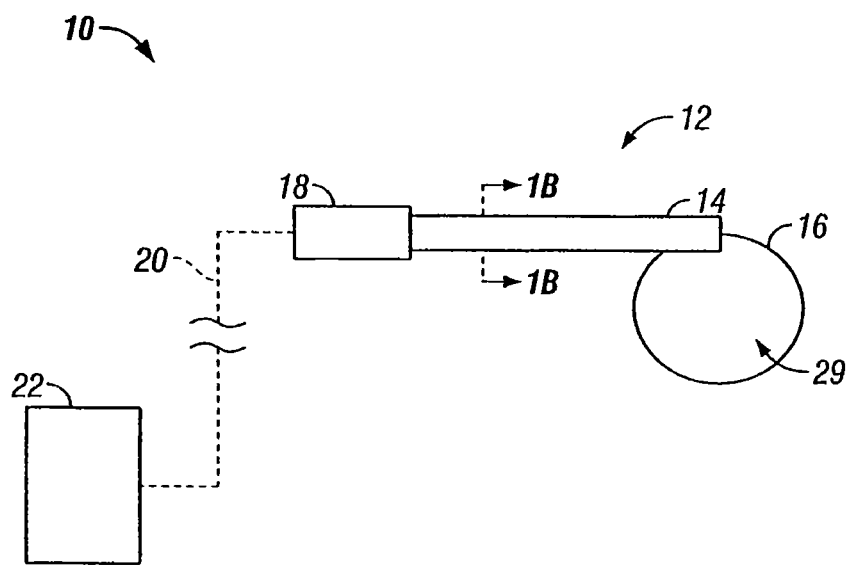
FIG. 1A shows a variation of a microwave antenna assembly having a curved antenna.

Microwave ablation devices typically ablate the tissue surrounding the antenna. The present invention clearly defines an ablation region by having the microwave antenna surround at least a majority of the tissue to be ablated without the need to actually penetrate or contact the ablated tissue. Furthermore, the curved microwave antenna allows for the direct control over the outer extent of the thermal lesion created by the device. FIG. 1A shows one variation in microwave antenna assembly 10 which preferably comprises at least microwave antenna 12 electrically connected to generator 22. Microwave antenna 12 preferably comprises shaft or feedline 14 with a distal end from which antenna or inner conductor 16 extends to define the ablation region 29, which is described in detail below. The proximal end of feedline 14 preferably comprises coupler 18 which electrically couples the antenna 12 to generator 22 via power transmission cable 20. The cable 20 is preferably a flexible cable which allows for the positioning of antenna 12 relative to a patient.

Figure 1B:
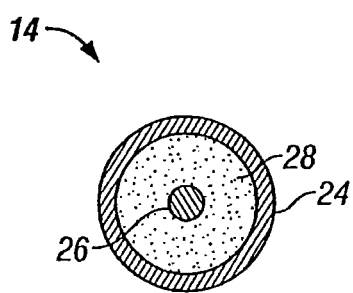
FIG. 1B shows a cross-section of the feedline from the antenna assembly of FIG. 1A.

Feedline 14 is preferably a coaxial cable, as shown by the cross-section 1B-1B in FIG. 1B taken from FIG. 1A. The feedline 14 may be formed of outer conductor 24 surrounding inner conductor 26. Conductors 24, 26 may be made of a conductive metal which may be semi-rigid or flexible. Most feedlines 14 may be constructed of copper, gold, or other conductive metals with similar conductivity values. Alternatively, feedline 14 may also be made from stainless steel which may additionally be plated with other materials, e.g., other conductive materials, to improve their properties, e.g., to improve conductivity or decrease energy loss, etc. A feedline 14, such as one made of stainless steel, preferably has an impedance of about $50\Omega$ and to improve its conductivity, the stainless steel may be coated with a layer of a conductive material such as copper or gold. Although stainless steel may not offer the same conductivity as other metals, it does offer strength required to puncture tissue and/or skin. A dielectric material 28 is preferably disposed between outer and inner conductors 24, 26, respectively, to provide insulation therebetween and may be comprised of any appropriate variety of conventional dielectric materials.

Figure 1D:
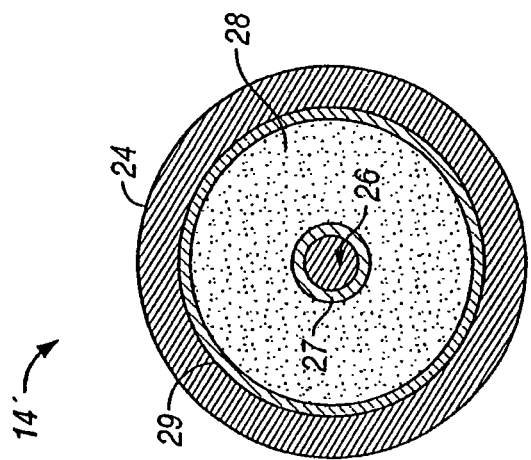
FIGS. 1C and 1D show cross-sectional and end views, respectively, of a variation of the feedline having plated conductive layers to increase energy transmission.
Figure 1C:
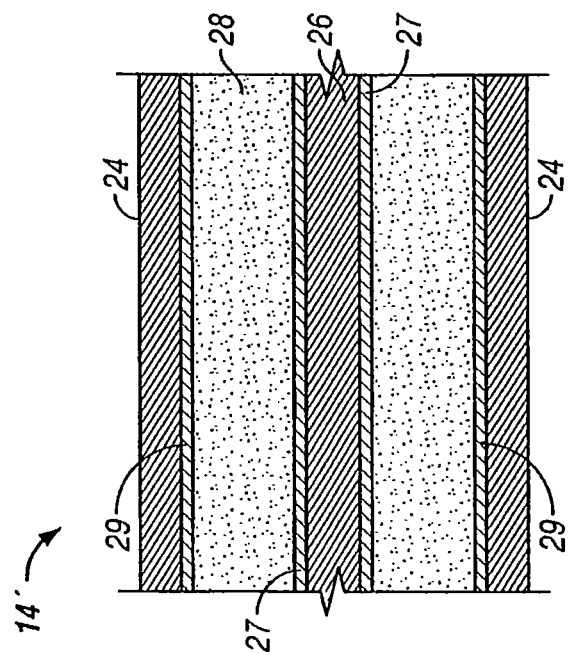

Furthermore, coaxial cables made from materials such as stainless steel may result in higher energy losses than other conductive materials, e.g. copper, gold, silver, etc. FIGS. 1C and 1D show cross-sectional and end views, respectively, of a variation of a feedline 14' which has conductive layers plated within to increase the energy transmission. As shown, the outer surface of inner conductor 26 may be plated with at least one additional conductive material described above in layer 27. Likewise, the inner surface of outer conductor 24 may be similarly plated with layer 29, which may be made of the same, similar, or different material as layer 27. The transmitted microwave energy is typically carried in the outer layers of inner conductor 26 so layer 27 need not be relatively thick.

Moreover, the addition of conductive layers 26 and/or 27 may not only increase energy transmission, but it may also aid in decreasing cable losses, decreasing cable heating, and distributing the overall temperature within the cable.

FIGS. 2A to 2G illustrate the different variations which the curved microwave antenna may embody. The size of the curved antenna portion may range anywhere from several millimeters to several centimeters, e.g., a 3 cm diameter or greater, depending upon the size of the tissue to be treated. The microwave antenna 12 may be used in various types of tissue, e.g., liver, breast, etc. In operation, microwave energy having a wavelength, k, is transmitted through microwave antenna 12 along feedline 14 and antenna 32. This energy is then radiated into the surrounding medium, e.g., tissue. The length of the antenna for efficient radiation may be dependent at least on the effective wavelength, $\lambda_{eff}$, which is dependent upon the dielectric properties of the medium being radiated into. Energy from microwave antenna 12 radiates and the surrounding medium is subsequently heated. A microwave antenna 12 through which microwave energy is transmitted at a wavelength, λ, may have differing effective wavelengths, $\lambda_{eff}$, depending upon the surrounding medium, e.g., liver tissue, as opposed to, e.g., breast tissue. Accordingly, to optimize the efficiency at which energy is radiated into the surrounding tissue, antenna length 32 may be varied to match according to the type of tissue surrounding the antenna. Also affecting the effective wavelength, $\lambda_{eff}$, are coatings and other structures, e.g., inflatable balloons, which may be disposed over microwave antenna 12, as discussed further below.

Figure 2A:
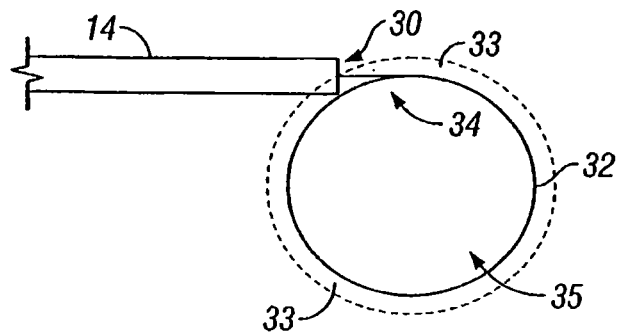
FIGS. 2A to 2G show different variations which the curved microwave antenna may embody.

Curved antenna 32 is seen in FIG. 2A extending from feedline 14 from feedline terminal end 30. Curved antenna 32 may either be attached to inner conductor 26, which is within feedline 14, through a variety of attachment methods (as described below) or antenna 32 may simply be an integral extension of inner conductor 26. Various conductive materials may be used to fabricate antenna 32, as above, and it may also be fabricated from shape memory alloys such as Nitinol. Alternatively, if a metal such as stainless steel is used, it may be biased to form the arcuate or curved shape as shown in the figures. Additionally, to help prevent energy from being conducted directly into contacting tissue, a dielectric coating may be placed over at least a majority of curved antenna 32. This coating may also aid in increasing the amount of radiated energy from antenna 32. Moreover, the coating is preferably lubricious to aid the insertion of antenna 32 into tissue as well as to aid in preventing tissue from sticking to antenna 32. The coating itself may be made from various conventional materials, e.g., polymers, etc.

The curved antenna 32 portion is preferably curved to form a loop or enclosure which is selectively formed large enough for surrounding a region of tissue, e.g., a lesion or tumor, to be radiated within the patient without making any contact with the tissue. Because no contact occurs between antenna 32 and the tumor, any danger of dragging or pulling cancerous cells along the antenna body into other parts of the body during insertion, treatment of the tissue, or removal of the antenna is eliminated. When microwave energy is delivered through feedline 14, curved antenna 32 and any part of the feedline or antenna 32 that completes the enclosure becomes part of the radiating portion. However, rather than radiating directly along the length of curved antenna 32, as one skilled in the art would normally expect, the curved configuration forms an ablation field or region 35 defined by curved antenna 32 and any tissue enclosed within ablation region 35 becomes irradiated by the microwave energy. Thus, because of the variability of antenna 32 and ablation region 35, the microwave antenna may be used to treat a variety of tissue size ranges and is not constrained by antenna delivery or deployment mechanisms. Any concurrent thermal effects may extend beyond the ablation region 35 outside curved antenna 32 by a short distance, e.g., a few millimeters to several millimeters. Accordingly, curved antenna 32 also defines a predictable region of tissue outside the irradiated zone which will also be irradiated. This margin 33 of tissue is generally very predictable and serves to treat the tissue the short distance outside the ablation region to ensure complete treatment of the area.

As previously mentioned, curved antenna 32 may be formed into a variety of shapes so long as antenna 32 preferably forms a substantially enclosed loop or enclosure, i.e., curved antenna 32 surrounds at least a majority of the tissue to be enclosed. Accordingly, antenna 32 may be formed into shapes such as circles, ellipses, spirals, helixes, squares, rectangles, triangles, etc., various other polygonal shapes, and partial forms of the various shapes so long as a majority of the enclosed tissue is surrounded. FIG. 2A shows antenna 32 formed into a complete loop in which distal tip 34 loops around to contact a proximal region of antenna 32 while clearly defining ablation region 35. The contact point between the two is preferably insulated such that no direct metal-to-metal contact occurs.

Figure 2B:
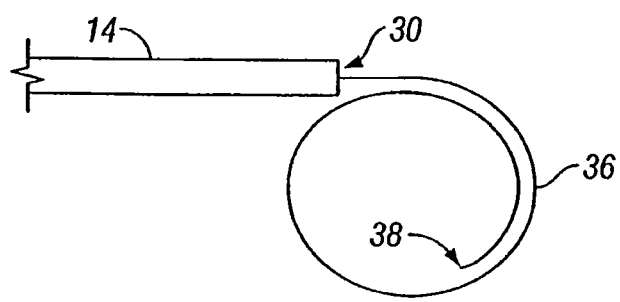

Another variation is shown in FIG. 2B in which distal tip 38 of curved antenna 36 is looped greater than 360° relative to feedline terminal end 30. The curved antenna may be looped or wound about the selected tissue region from about 180° (relative to a central point defined by the curved antenna), where the tissue is just surrounded or partially enclosed by the antenna, to multiple loops where the tissue is surrounded numerous times by the antenna. Separation between the individual loops is shown for clarity and is not intended to be limiting since contact between the loops may occur. The number of times which the tissue is surrounded may be correlated to the desired radiation effects, as discussed in further detail below.

Figure 2C:
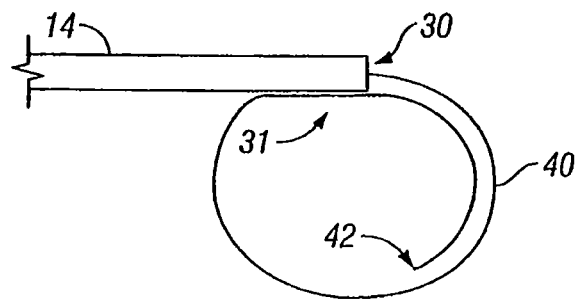
Figure 2D:
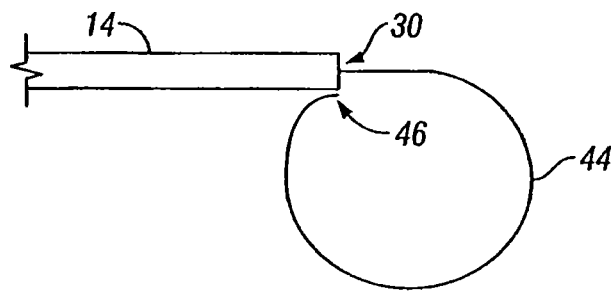
Figure 2E:
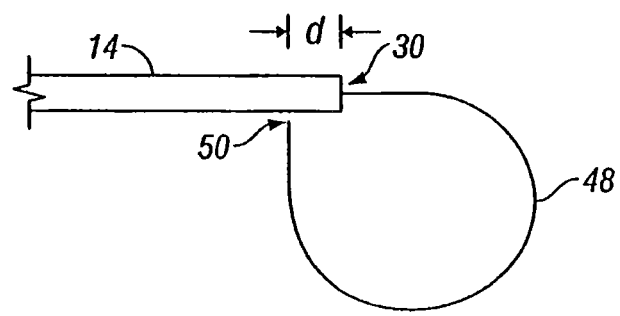
Figure 2F:
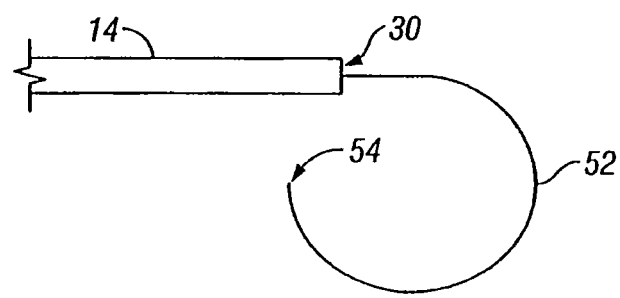

FIG. 2C shows another variation in which distal tip 42 of curved antenna 40 is wound greater than 360° relative to feedline terminal end 30 but where antenna 40 is formed into a more elliptical shape. In this variation, antenna 40 forms overlapping region 31 with a distal portion of feedline 14. In such an overlapping area, overlap region 31 of feedline 14 may form part of antenna 40. FIGS. 2D to 2F show the distal tips 46, 50, 54 of each of curved antennas 44, 48, 52, respectively, with various degrees of enclosure. Although numerous different shapes and partial shapes may be utilized, the enclosure is preferably formed in a looped configuration with at least a partial overlap between the distal tip and either a portion of the feedline 14 or with the antenna itself. If the overlap is formed with feedline 14, as shown in FIG. 2D, a portion of feedline 14 itself may act as part of the antenna 44 when power is applied. If a separation exists between distal tip 50 and feedline terminal end 30, as shown in FIG. 2E, then a distance, d, between the two is preferably less than 3 cm, and more preferably less than 1 cm such that an ablation region is clearly defined by the antenna. Accordingly, feedline 14 over the distance, d, may form part of the radiating antenna 48 in such a configuration. Otherwise, various other shapes or partial shapes may be utilized.

Figure 2G:
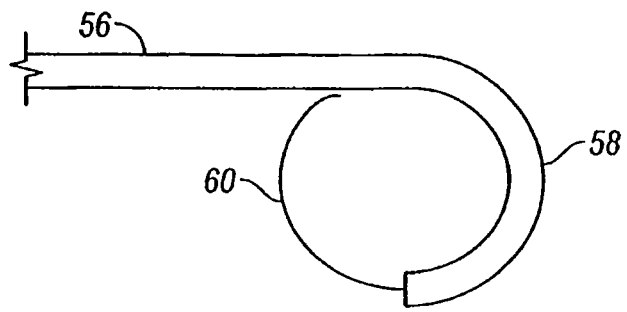

An alternative variation is shown in FIG. 2G where feedline 56 is extended into a curved portion 58 to partially define the ablation region. Curved antenna 60 may be used to complete the enclosure. Curved portion 58 is shown forming an arc of about 180°, but it may be formed into any curved portion with varying degrees of curvature to partially form the ablation region.

An optional method for optimizing the length of the antenna to the target tissue site may involve adjusting the length of the antenna itself to optimize the amount of microwave energy which is delivered to specific tissue types such that the effective wavelength, $\lambda_{eff}$, is matched to the surrounding tissue medium type. For instance, depending upon the tissue type, the microwave antenna may be shortened in length to increase the frequency with which the energy is delivered efficiently. Alternatively, antenna length may also be shortened to decrease the frequency as certain frequencies are more efficient at delivering energy in certain tissue types.

Shorter antenna lengths may easily be inserted within the matching tissue type with relative ease; however, longer antenna lengths may present a challenge in deployment and placement within the tissue. One method of adjusting for antenna length is seen in the variation shown in FIG. 2H. Curved antenna 61 extends from feedline 14, as in other variations, but has an additional distal portion 63 which doubles back around curved antenna 61 from tip 62. Distal antenna portion 63 may lie within the same plane as curved antenna 61 or it may optionally be positioned at an angle relative to antenna 61. In either case, tip 62 may be configured to have a cutting edge to facilitate insertion into the tissue, or it may also be optionally configured to provide an RF energy cutting tip, which is described in greater detail below.

Figure 2H:
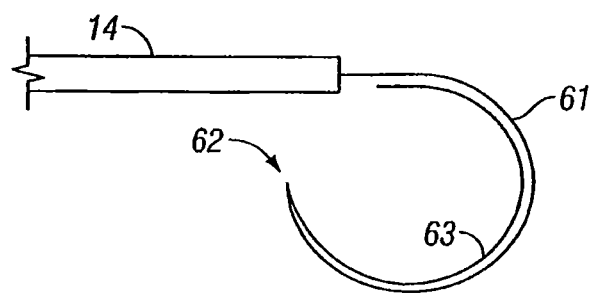
FIGS. 2H to 2M show different variations of the microwave antenna with variable antenna lengths.
Figure 2I:
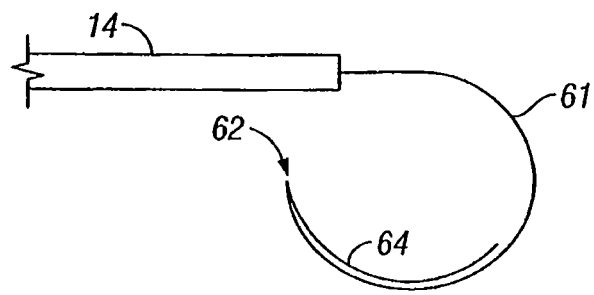
Figure 2J:
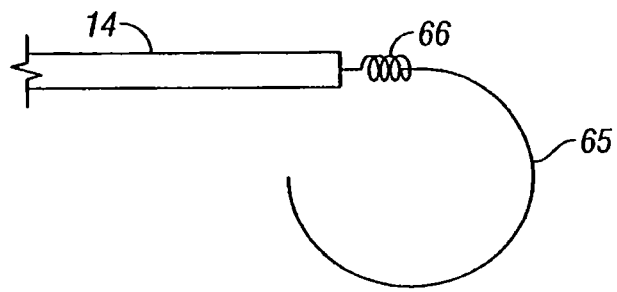

While distal antenna portion 63 is shown in FIG. 2H as doubling back along nearly the entire length of curved antenna 61, it may be sized to any practical length to match the tissue type. For instance, FIG. 2I shows a variation in which distal antenna portion 64 extends back from tip 62 only partially along the length of curved antenna 61. Another variation is shown in FIG. 2J in which curved antenna 65 has a looped portion 66 extending partially along the length of curved antenna 65. Looped portion 66 may be any appropriate length of antenna which is simply formed into a looped or coiled structure. The portion 66 may also be located anywhere along the length of curved antenna 65.

Figure 2K:
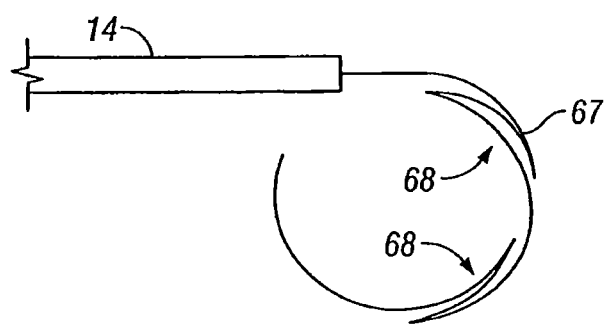
Figure 2L:
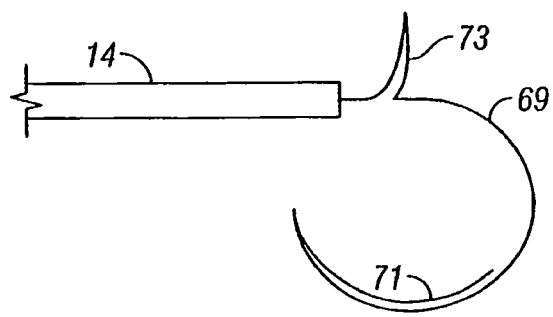

Additional variations are shown in FIGS. 2K and 2L in which any number of double-back portions of the antenna may be formed. FIG. 2K shows curved antenna 67 with two doubled portions 68 along its length. This variation is not limited by the number of doubled portions but may include any number as necessary to achieve the desired radiative and geometric effects. FIG. 2L shows another variation in which curved antenna 69 has a distal portion 71 doubling back along antenna 69, and which also has an additional proximal portion 73 formed in another plane relative to the plane formed by antenna 69.

Figure 2M:
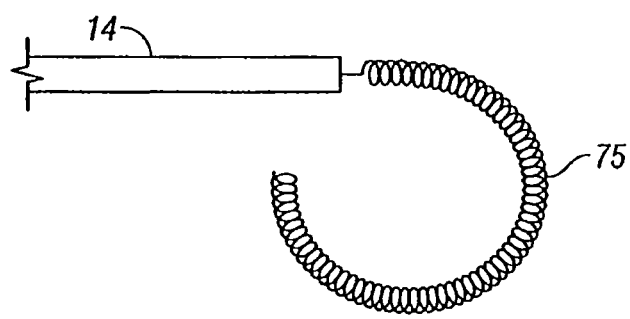

FIG. 2M shows a variation which is similar to that shown in FIG. 2J but in which the antenna is formed entirely into a looped or coiled antenna 75. The coiled antenna 75 may have a coil diameter which is uniform along the length of antenna 75 or it may optionally have a variable coil diameter along its length. The coiled antenna 75 allows for a microwave antenna having a relatively large antenna length constrained within an area no larger than some of the other variations described herein.

Figure 2N:
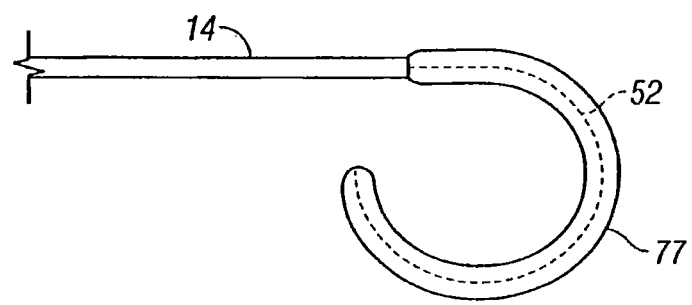
FIG. 2N shows a variation of the microwave antenna having an inflatable balloon disposed about the curved antenna for changing the effective microwave wavelength.

As discussed above, the effective wavelength, $\lambda_{\text{eff}}$, of the microwave radiation may also be affected, aside from antenna length, by coatings and other structures which may be disposed over the microwave antenna. Accordingly, a layer of insulative material may be varied in thickness over at least a majority of the length of the curved antenna to achieve a matched effective wavelength. Alternatively, an inflatable balloon 77 may be disposed over the length of curved antenna 52, as shown in FIG. 2N to also match the effective wavelength. Balloon 77 may be in a deflated state during the deployment of antenna 52 within the tissue. Once antenna 52 has been desirably positioned, balloon 77 may be filled with a liquid, e.g., saline, water, etc., until it has inflated sufficiently about antenna 52. The size of balloon 77 may be varied according to the desired radiative effects, the length of antenna 52, as well as the type of tissue which the antenna 52 will be inserted within.

Figure 2O:
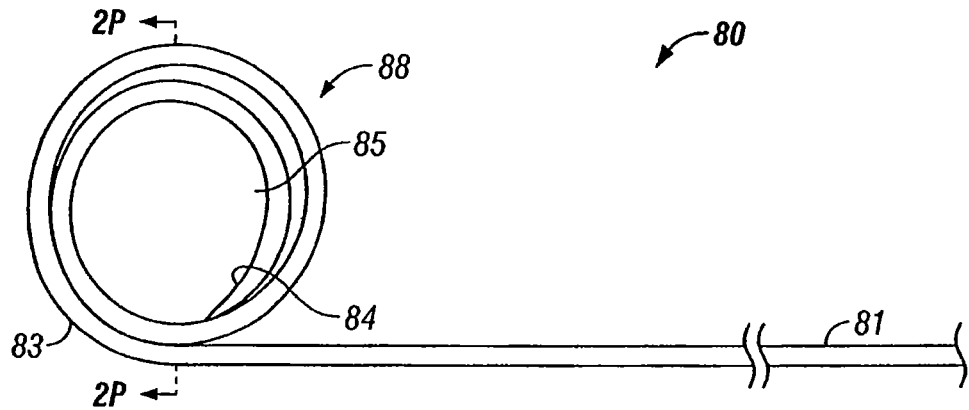
FIGS. 2O and 2P show another variation of the microwave antenna having a helical antenna portion.
Figure 2P:
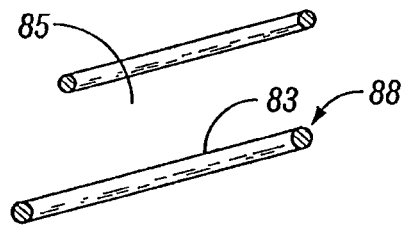
Figure 2Q:
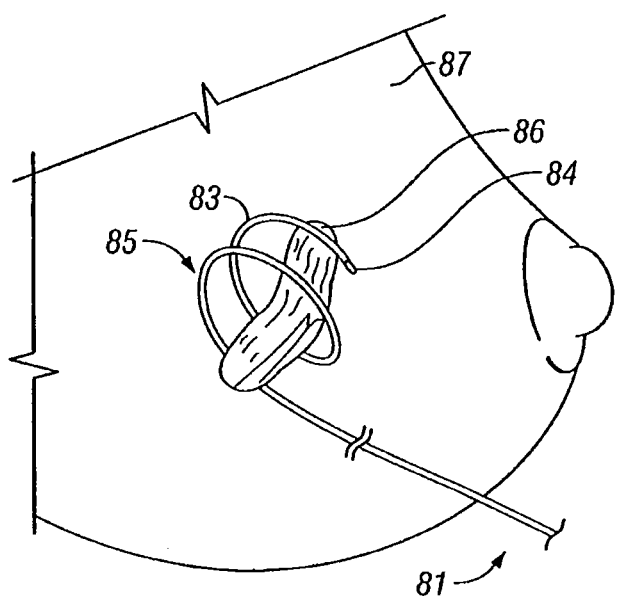
FIG. 2Q shows the antenna variation from FIGS. 2O and 2P inserted into breast tissue and surrounding a tumor.

As described above, an antenna may be looped about the region of tissue to be ablated any number of times. The multiple coils or loops may all be wound within the same plane or alternatively, they may be wound in a spiral or helical configuration. FIGS. 2O to 2Q show a variation in which a helically configured antenna 80 may comprise a straightened portion or feedline 81 and a helical portion 88 which is insertable within the tissue. FIG. 2O shows a top view of a variation on the antenna 80 which is similar in configuration to the device shown and described in U.S. Pat. No. 5,221,269 to Miller et al., which has been incorporated above by reference in its entirety. As seen in this variation, helical portion 88 comprises antenna 83 which is configured into a tapering helical pattern to form an ablation region 85 within the helical portion 88, as better shown in the cross-section 2P-2P in FIG. 2P. Antenna 83 may terminate in a tapered distal tip 84 to facilitate antenna entry into the tissue. Helical portion 88 may alternatively be formed into a coiled section in which multiple coils are formed with a uniform diameter. The number of coils antenna 83 forms may be determined by the optimal antenna length desired according to the tissue type being treated, as described above in detail.

As seen in FIG. 2Q, antenna 83 is shown as having been inserted into breast 87 to treat tumor 86. Antenna 83 may be inserted within breast 87 in an uncoiled and straightened configuration through an introducer (not shown). Antenna 83 is preferably made from a shape memory alloy, e.g., Nitinol or some other similar alloy, such that as distal tip 84 is inserted within the tissue, it may be preconfigured to form the helical shape as antenna 83 is further inserted within the tissue. As antenna 83 is advanced, distal tip 84 may form the helical shape about the tumor 86, or some region of tissue to be ablated, within the formed ablation region 85.

Figure 3A:
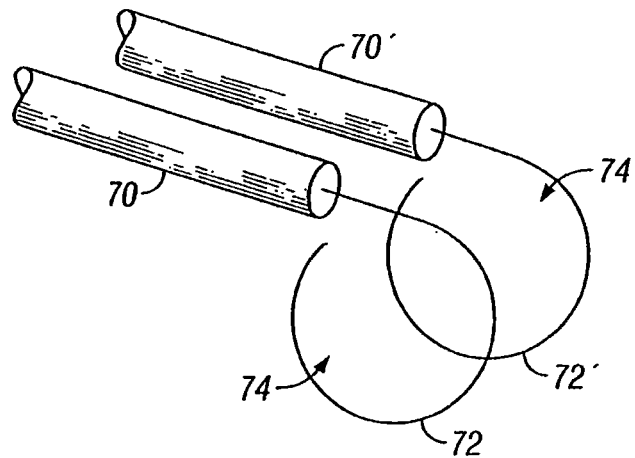
FIG. 3A shows one variation for using multiple curved antennas which are adjacent to one another.
Figure 3B:
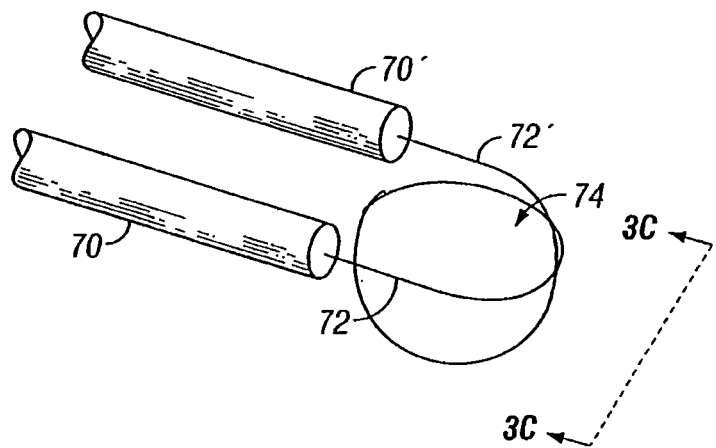
FIGS. 3B and 3C show isometric and end views, respectively, of another variation for using multiple curved antennas to form a cage-like ablation device.
Figure 3C:
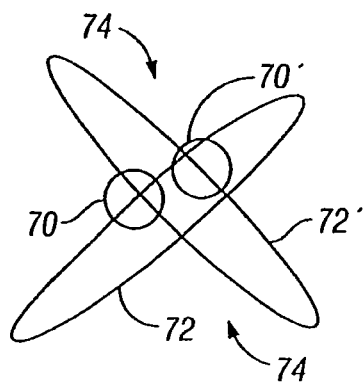

To ablate larger regions of tissue, multiple microwave antennas may be used in conjunction with one another. FIG. 3A shows two antennas, first feedline 70 and second feedline 70', positioned adjacent to one another such that their respective antennas, first antenna 72 and second antenna 72', are positioned to ablate a larger region of tissue over a distance within their combined ablation regions 74. Another variation using two antennas is shown in FIGS. 3B and 3C in which first and second feedlines 70, 70' are positioned adjacent to one another with their respective antenna portions 72, 72' being positioned to interloop with one another. FIG. 3C shows an end view of FIG. 3B in which the interlooped antennas 72, 72' may be seen to form ablation region 74 within the combined areas of the antennas. The caged ablation region 74 is effective in completely encapsulating a region of tissue to be ablated within a spherical ablation region. Other shapes, e.g., spheroid, ovoid, ellipsoid, etc., may alternatively be formed by a combination of the two antennas 72, 72' positioned appropriately or any number of antennas as practical or desired.

Alternatively, first and second feedlines 70, 70' may be positioned to approach the region of tissue to be ablated from different locations and at different angles, as seen in FIG. 4, such that the combined effect of the first and second antennas 72, 72' may form a complete loop or shape and ensures complete coverage of the ablation region 76. In either of these variations, any number of antennas may be used as practicable depending upon the size of the tissue to be ablated as well as the desired effect from the ablation.

Alternatively, a single feedline 78 having multiple antennas 80 which define an ablation region 82 over some distance may be utilized, as seen in the FIG. 5A. In this variation, a plurality of antennas, i.e., two or more, may extend from a single feedline 78 to form an enlarged ablation region. Because a single feedline is used, a single incision in a patient is required while a relatively large area of tissue may be ablated with the single device. FIG. 5B shows an end view of the variation from FIG. 5A and shows the multiple antennas 80 extending from the single feedline 78. Multiple antennas 80 may be positioned in any variety of configurations relative to one another depending upon the areas of tissue to be ablated.

Alternative embodiments which may be utilized for forming caged ablation regions using multiple antennas may be seen in PCT publication WO 01/60235 to Fogarty et al. entitled "Improved Device for Accurately Marking Tissue", which is incorporated herein by reference in its entirety. Similarly, multiple antennas may be used to form caged embodiments for surrounding tissue within an ablation region using configurations similar to the tissue marking devices described in the publication.

Figure 6C:
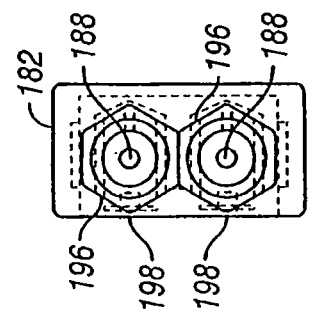
FIGS. 6A to 6C show side, top, and end views, respectively, of an antenna guide assembly variation which may be used to align microwave antennas.
Figure 6A:
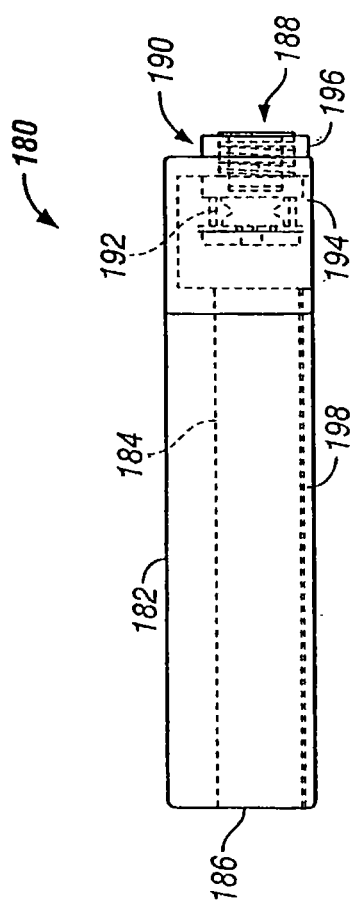

To assist in aligning multiple antennas for ablating larger regions of tissue, various alignment guides may be used to provide for uniform or consistent antenna placement within the tissue to be treated. One variation may be seen in FIGS. 6A to 6C which shows side, top, and end views, respectively, of antenna guide assembly 180. Guide assembly 180 may be used to align microwave antennas parallel to each other in one variation as shown in FIG. 3A. In use, a distal end of a microwave antenna may be advanced through proximal entry 186 of guide assembly 180, through guide passage 184 and out through distal port 188 such that a portion of the microwave antenna extends beyond distal port 188 for insertion into the tissue region to be treated. The antenna may be releasably locked into position within guide assembly 180 by locking assembly 190.

The guide assembly 180 itself may be comprised of guide body 182, which may be made as an integral unit from a variety of materials, e.g., various polymers or plastics, etc. Guide body 182 may have an outer surface configured to be held by a surgeon or physician. Within the guide body 182, one or more guide passages 184 may be defined through the length of guide body 182 for holding and aligning the microwave antennas. Although this variation shows two passages 184 for aligning two antennas, this is merely illustrative and other variations may be employed for aligning any number of antennas as practicable, e.g., a single antenna or three or more.

As further shown, guide body 182 also defines proximal entry 186 through which the antennas may be advanced into passages 184 and through distal ports 188. The antennas may be further positioned through locking assembly 190 located within guide body 182 and used to temporarily lock the antennas in place. The antennas may be locked within assembly 190 by locking mechanism 192 which may be keyed to lock against the antenna. To release a locked antenna, locking assembly 190 may further have release latches 194 which are configured to release locking mechanism 192 to release the antenna. Locking assembly 190 may be held in place within guide body 182 by retaining members 196, which may be configured as threaded or snap-fit members for engagingly attaching onto a portion of locking assembly 190.

Figure 6B:
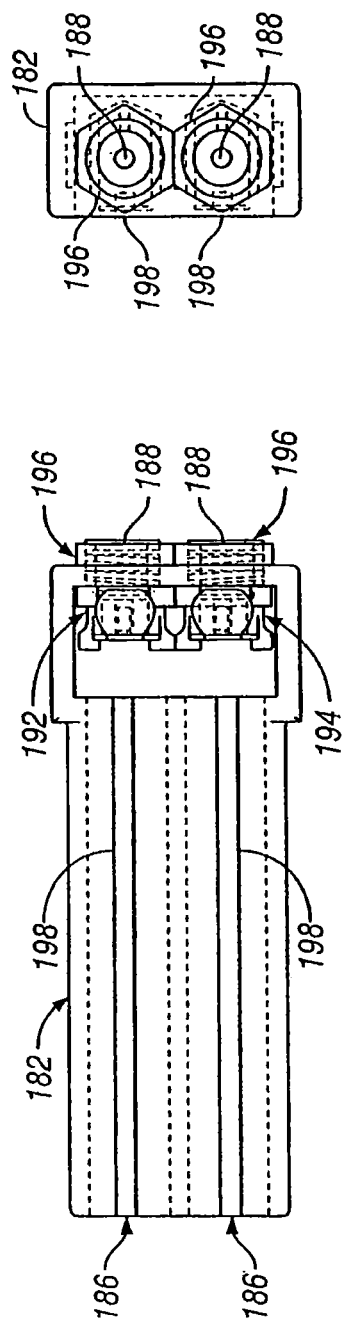

To align the microwave antennas with guide assembly 180, guide body 182 may define longitudinal alignment channels 198 along the lengths of each guide passage 184. Alignment channels 198 may extend through guide body 182 from guide passages 194 to the outer surface of guide body 182 and they may be aligned parallel to each other along the length of guide assembly 180, as shown in FIG. 6B. The microwave antennas used with guide assembly 180 may be configured to have a corresponding protrusion (not shown) extending from the feedline body and the protrusion may be keyed to align with and travel through alignment channels 198. It is the alignment of the keyed antenna with the alignment channels 198 which may force the antennas to desirably align with each other such that the looped antennas extend parallel to one another.

Figure 7A:
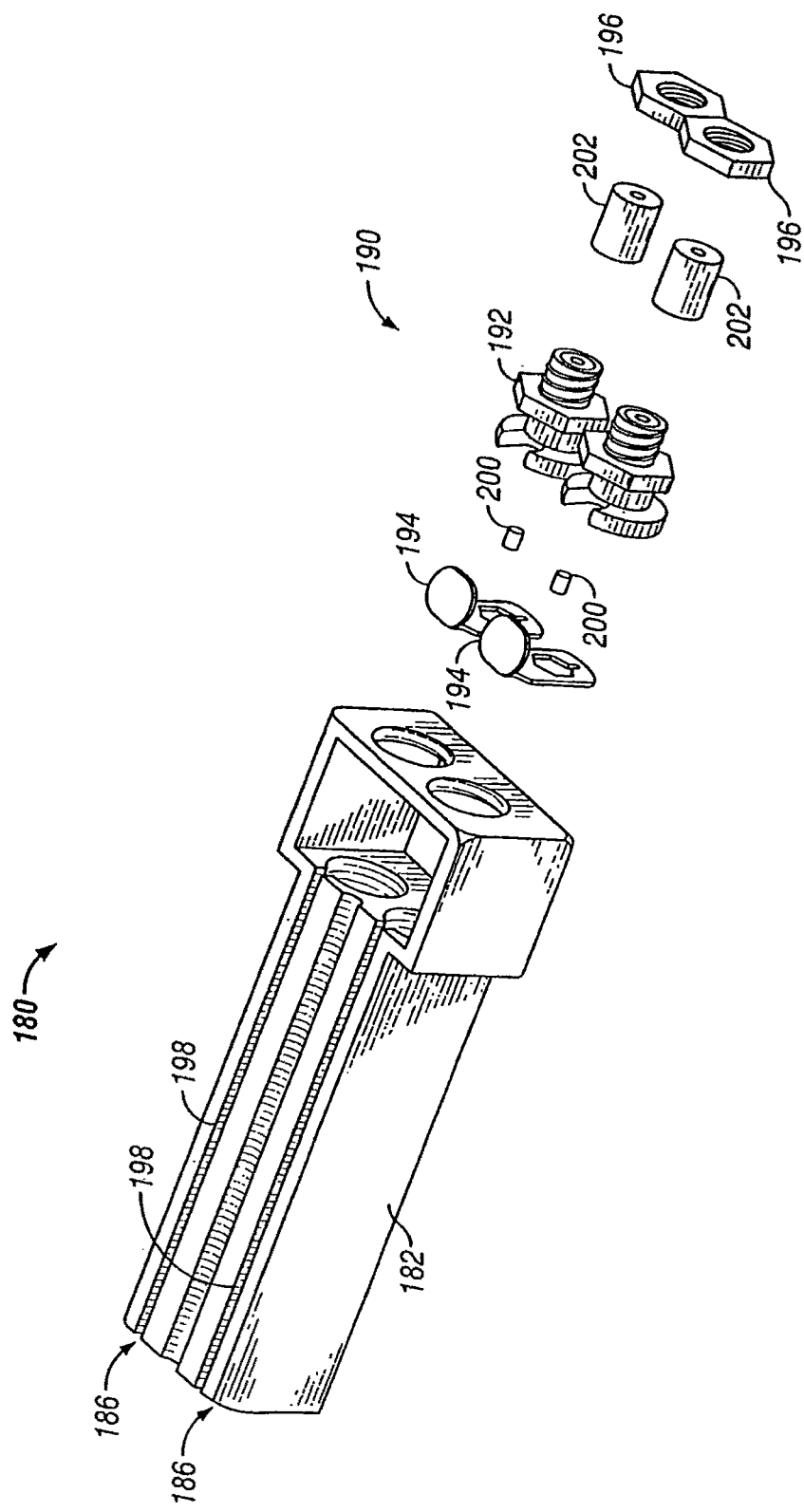
FIGS. 7A and 7B show isometric exploded and assembly views, respectively, of the guide assembly variation of FIGS. 6A to 6C.
Figure 7B:
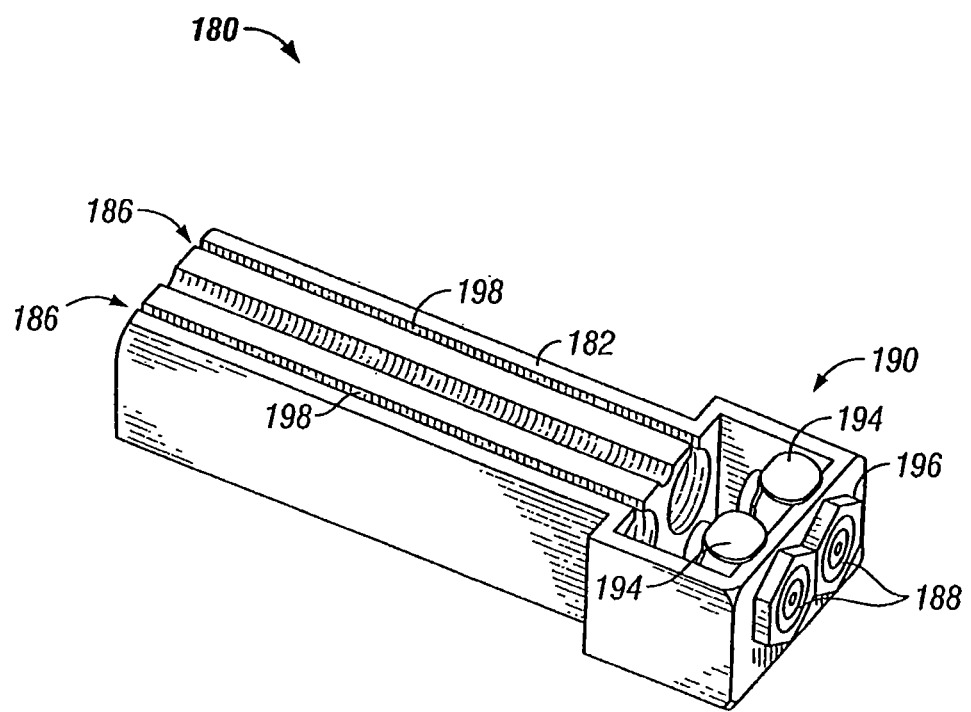

FIGS. 7A and 7B show isometric exploded and assembly views, respectively, of guide assembly 180. The exploded view in FIG. 7A shows release latches 194 aligned with locking mechanism 192. Latches 194 may be aligned and held in position with pins 200 relative to mechanism 192. Ferrules 202 may also be used for placement within locking mechanism 192 to facilitate antenna alignment.

Figure 8A:
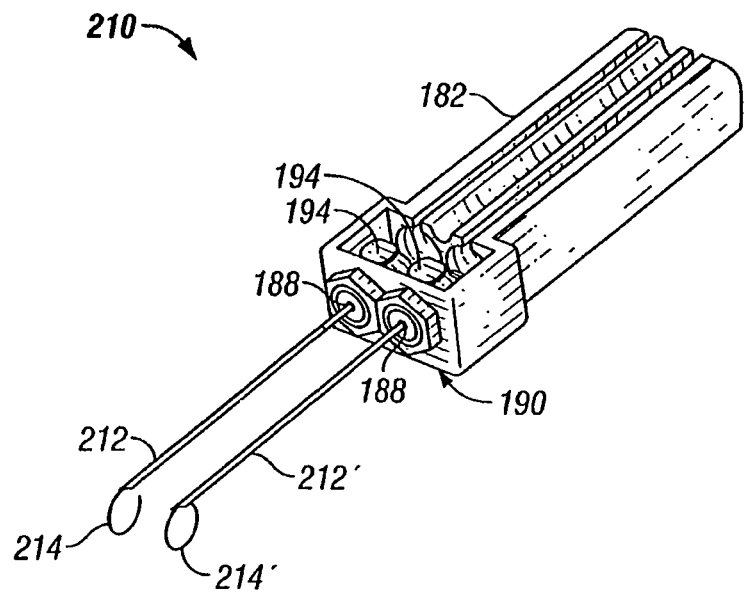
FIGS. 8A and 8B show isometric and end views, respectively, of the antenna guide assembly of FIGS. 6A to 6C having microwave antennas positioned within.
Figure 8B:
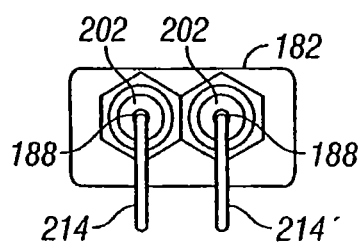

FIGS. 8A and 8B show isometric and end views, respectively, of antenna and guide assembly 210. First 212 and second 212' antenna feedlines are shown in this variation as having been positioned within guide body 182 such that first 214 and second 214' looped antennas are parallel to one another. As shown in FIG. 8B, antennas 214, 214' may be positioned and maintained in this parallel manner for treatment of regions within tissue. Although shown in this variation as having parallel antennas, the possible orientations of the antennas are not so limited. Other relative positions for the antennas may be utilized depending upon the desired effects.

Another variation for facilitating antenna positioning is shown in FIGS. 9A to 9C. In this variation, antenna guide assembly 220 similarly has guide body 222 with guide passages 224 defined throughout the assembly 220 and ending in distal port 232 through which microwave antennas may be positioned. Locking assembly 226 may also similarly comprise locking mechanism 228 for temporarily locking the antennas into position. Locking mechanism 228 is located within guide body 222 and held thereto via retaining members 236, which may be any of the retaining members as described above. Release latch 230 may be used to release locking mechanism 228 for releasing locked antennas. This variation 220, however, may be used when the antennas are desirably angled relative to one another, similar to the antenna placement variation shown in FIGS. 3B and 3C. Accordingly, alignment channels 234 may be formed within guide body 222 such that the channels 234 are angled away relative to each other.

Figure 10A:
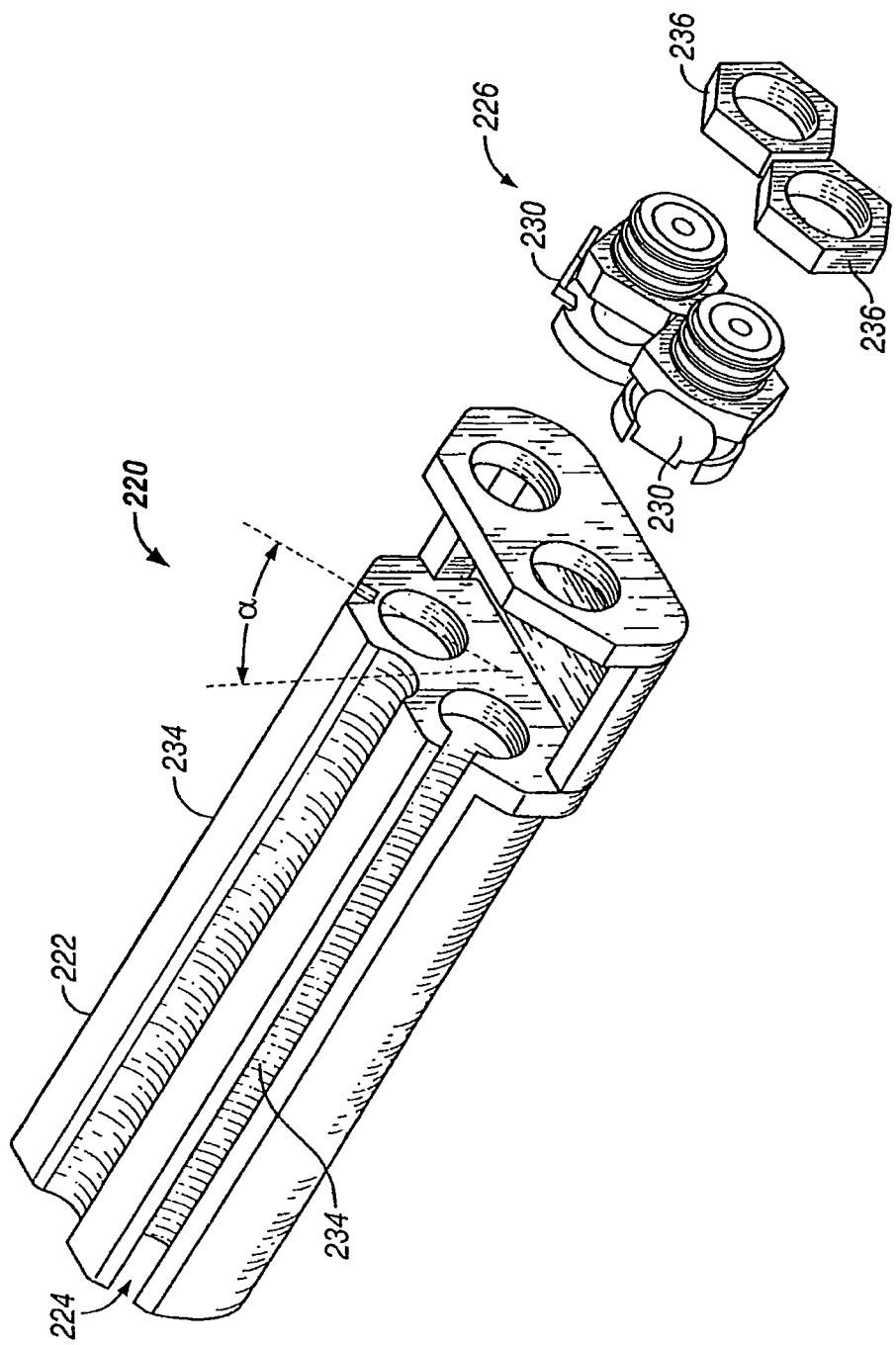
FIGS. 10A and 10B show isometric exploded and assembly views, respectively, of the guide assembly variation of FIGS. 9A to 9C.
Figure 10B:
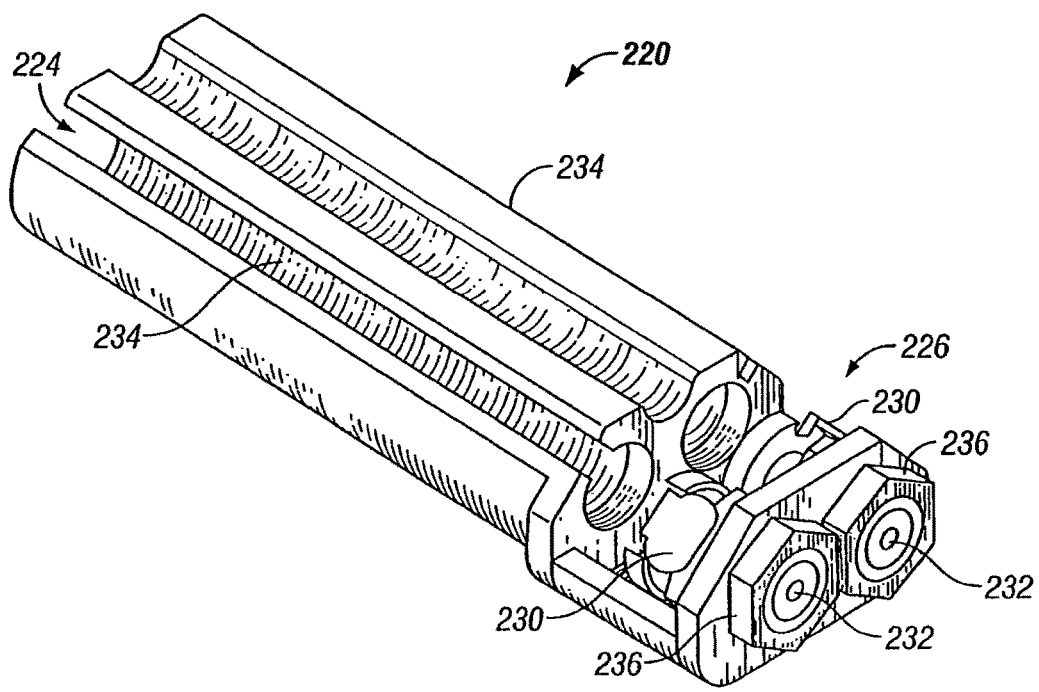

As shown in FIGS. 10A and 10B, which are isometric exploded and assembly views, respectively, of guide assembly 220, alignment channels 234 may be angled relative to one another such that they are angled away. Both or either channel 234 may be angled at various angles, α, depending upon the desired antenna positioning, e.g., 30°, 45°, etc. Alternatively, they may be angled towards one another as practicable.

FIGS. 11A and 11B show isometric and end views, respectively, of antenna and guide assembly 240. The antennas used with this guide variation may also be configured to have protrusions such that they are keyed to align within the channels 234 at specified angles. For instance, as shown in FIG. 11A, first 242 and second 242' feedlines may be positioned through guide body 234 such that first 244 and second 244' antennas are interlooped with one another to form an enclosed ablation region, as described above. Depending upon the angle at which either or both antennas 244, 244' are positioned relative to one another, a variety of shapes may be formed by the antennas, as further discussed above.

Figure 12A:
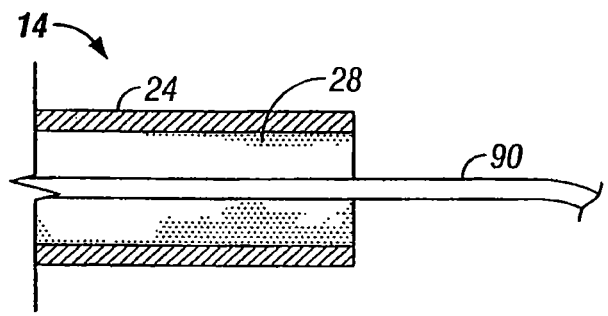
FIGS. 12A to 12C show variations on different methods of attaching a curved microwave antenna.

As further mentioned above, the curved antenna may either be attached to the inner conductor, which is disposed within the feedline, through various attachment methods or the antenna may simply be an integral extension of the inner conductor. FIG. 12A shows a cross-sectioned side view of the terminal end of feedline 14. As seen, outer conductor 24 surrounds inner conductor 90 and is separated by dielectric 28. The point where inner conductor 90 begins to form the curved antenna, outer conductor 24 and dielectric 28 end while inner conductor 90 continues on to form an integrally attached antenna.

Figure 12B:
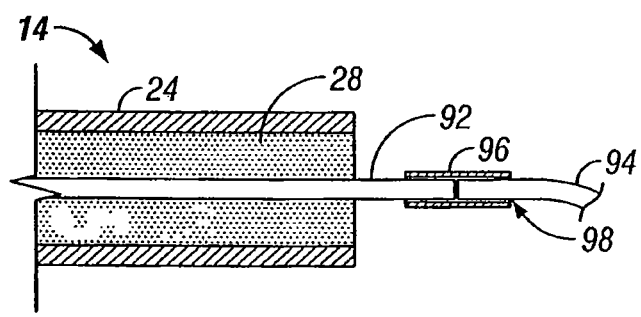

An alternative variation is seen in FIG. 12B in which a separate antenna 94 is mechanically affixed or attached to inner conductor 92, which may extend partially from outer conductor 24. The mechanical connection between antenna 94 and inner conductor 92 may be accomplished by a variety of methods, only a few of which are described herein. Connector 96 may be used to electrically and mechanically join each of the terminal ends of inner conductor 92 to antenna 94 through connector lumen 98, e.g., by a simple mechanical joint, or by soldering both ends together and additionally soldering connector 96 over the joint. Aside from solder, a conductive adhesive may similarly be used. Alternatively, each of the terminal ends may be crimped together by connector 96.

Figure 12C:
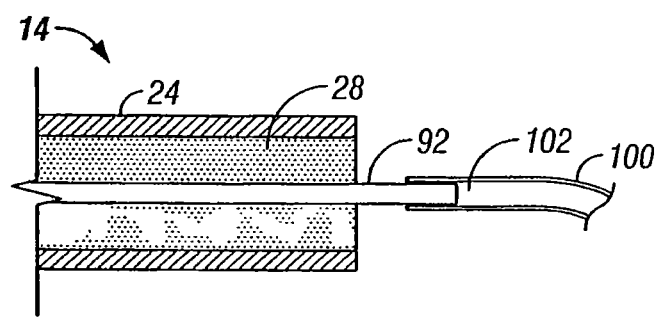

Another variation may have each of the terminal ends threaded in opposite directions so that inner conductor 92 may be screwed into connection with antenna 94 via a threaded connector lumen 98. If a separate antenna is utilized, then one made from the same material as inner conductor 92 may be used. Alternatively, an antenna 94 made from a shape memory alloy, e.g., Ni—Ti alloy (Nitinol), may be attached. However, any oxide layers which may form on the surface of the shape memory alloy is preferably removed by using, e.g., a reamer, prior to attachment. An alternative attachment which may be utilized is shown in FIG. 12C in which a tubular antenna 100 having an antenna lumen 102 may be attached to inner conductor 92 by partially inserting the conductor 92 within lumen 102 prior to mechanical fixation. The tubular antenna 100 may then be similarly attached to inner conductor 92 using the various methods described above, e.g., soldering, crimping, adhesives, etc.

Figure 13A:
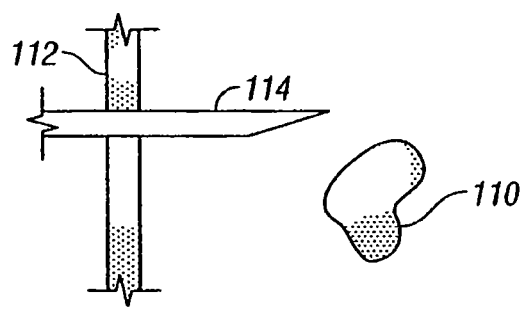
FIGS. 13A to 13G show one variation on deploying and positioning a curved microwave antenna about a tissue region of interest.
Figure 13B:
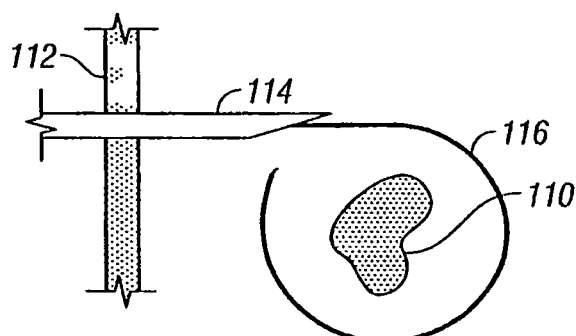

Insertion and placement of the microwave antenna within the body of a patient may be accomplished through one of several different methods. One method is shown in FIGS. 13A to 13G, which show the deployment and placement of a microwave antenna about a region of tissue to be ablated. Once a region of diseased tissue, e.g., a tumor, has been located within a patient's body, e.g., within the breast or the liver, a microwave antenna may be deployed in vivo to effect treatment. As seen in FIG. 13A, introducer 114 may be inserted through skin surface 112 in an area adjacent to the tumor 110. Wire 116, which may be held within introducer 114 during insertion or inserted afterwards, may then be advanced through introducer 114 and through the tissue surrounding tumor 110. Wire 116 is preferably made of a shape memory alloy which is preformed to have a curvature in any of the shapes described herein, although it is shown in the figure as a circular loop. This curvature is selectively preformed such that wire 116 is able to at least substantially surround tumor 110 while being advanced without contacting the exterior of tumor 110.

Figure 13C:
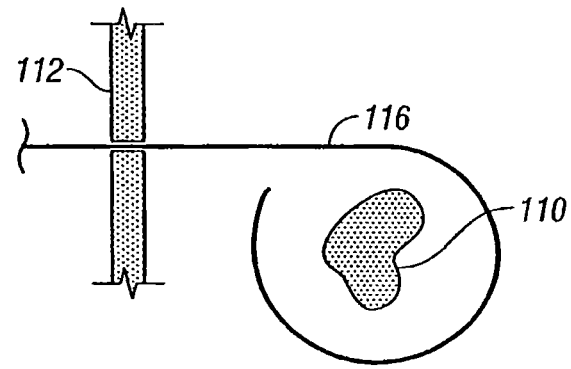
Figure 13D:
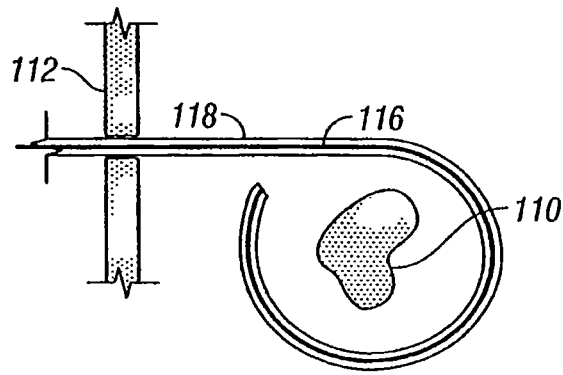
Figure 13E:
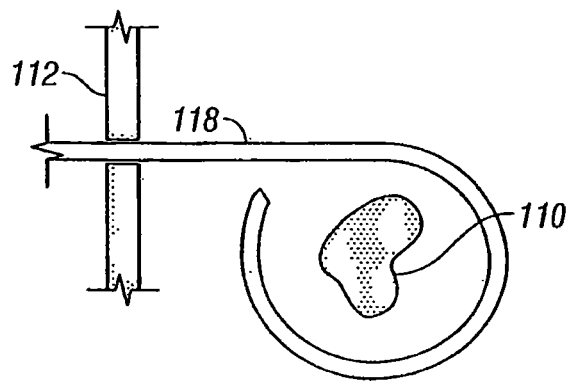
Figure 13F:
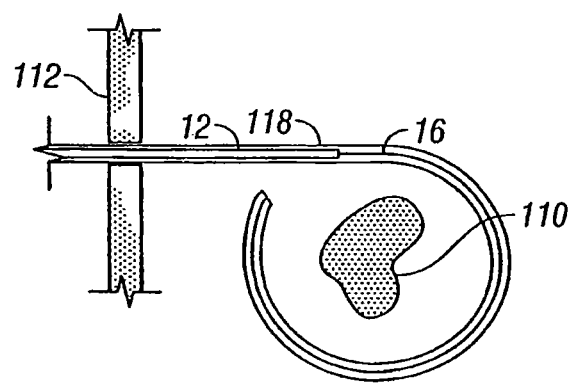
Figure 13G:
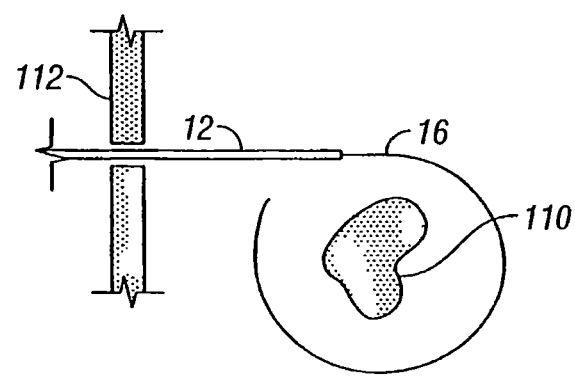

Once wire 116 has been desirably positioned around tumor 110, introducer 114 may be removed from the tissue area while maintaining the position of wire 116, as shown in FIG. 13C. Then, as shown in FIG. 13D, a flexible guide tube 118 may be advanced over wire 116 preferably all the way to the distal tip of wire 116. Once tube 118 has been positioned, wire 116 may then be withdrawn, as seen in FIG. 13E, and microwave antenna 12 may be advanced within tube 118 such that antenna 16 substantially surrounds tumor 110, as seen in FIG. 13F. Then tube 118 may be withdrawn from the area while maintaining the position of microwave antenna 12 about tumor 110 for treatment to be effectuated, as seen in FIG. 13G.

Figure 14A:
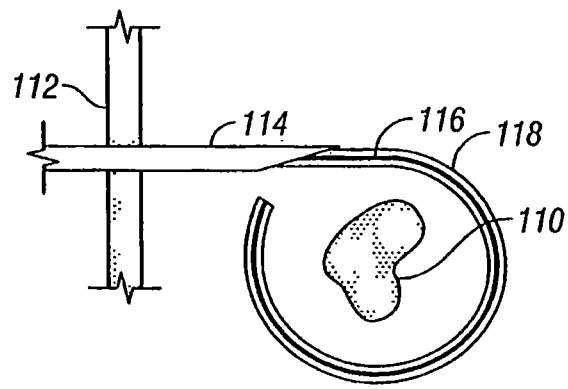
FIGS. 14A and 14B show another variation on deploying the curved microwave antenna about a tissue region of interest in which a wire and tube member may be deployed simultaneously.
Figure 14B:
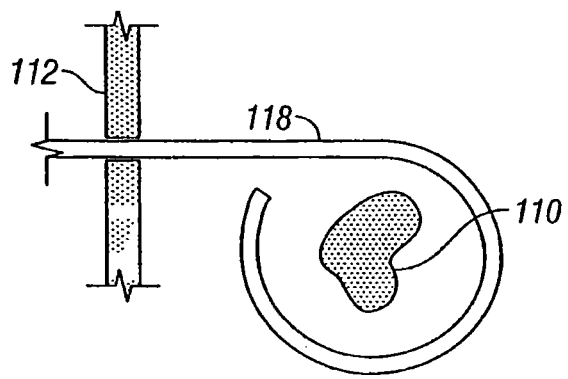

An alternative method of deployment is shown in FIGS. 14A and 14B. Introducer 114 may be positioned as above, but wire 116 and tube 118 may be deployed simultaneously rather than sequentially, as seen in FIG. 14A. Once the two have been desirably positioned, wire 116 may be withdrawn from tube 118, as shown in FIG. 14B, and the microwave antenna 12 may be inserted and positioned as above.

Figure 14C:
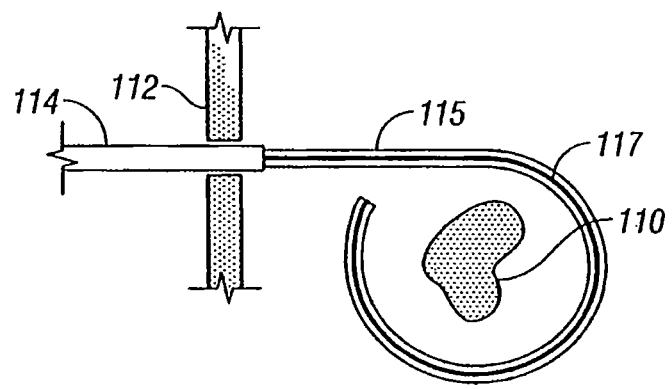
FIG. 14C shows another variation on deploying the curved microwave antenna about a tissue region of interest in which the inner conductor and dielectric coating may be deployed together as a single unit within the tissue.

Another variation for deployment is shown in FIG. 14C where once introducer 114 has been positioned through skin surface 112, or some other tissue interface, inner conductor 117 surrounded by dielectric 115 may be advanced together through the tissue to enclose tumor 110 within an ablation region. As such, inner conductor 117 and dielectric 115 may be integrally formed into a single unit; alternatively, inner conductor 117 may be slideably disposed within dielectric 115 but advanced simultaneously. The introducer 114 in this variation may be adapted to be used as an outer conductor during microwave energy transmission through the device.

Figure 15A:
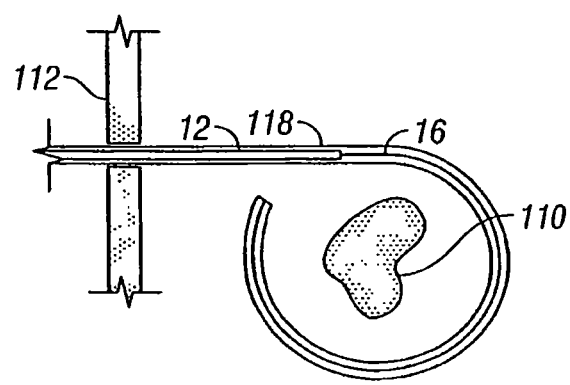
FIGS. 15A and 15B show another variation on deploying the curved microwave antenna about a tissue region of interest in which the tube member may be used as an insulator during microwave treatment.
Figure 15B:
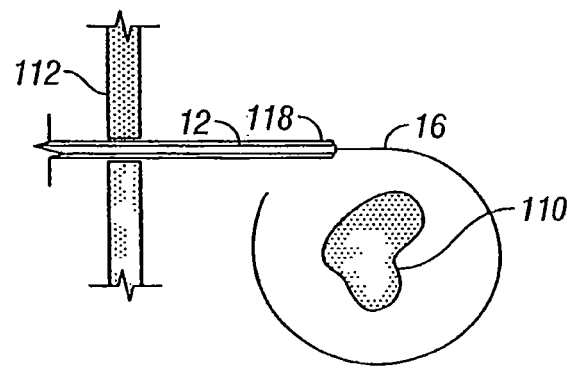

Another variation for deployment and use of the microwave antenna 12 is shown in FIGS. 15A and 15B. Microwave antenna 12 may be positioned within tube 118, as above and as in FIG. 15A. However, rather than withdrawing tube 118 entirely from the tissue, it may be partially withdrawn until it covers only the feedline of microwave antenna 12 such that it may be used as an insulator between the shaft or feedline and the surrounding tissue, as shown in FIG. 15B.

Figure 15C:
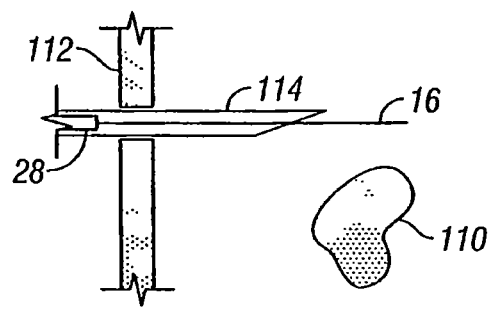
FIGS. 15C and 15D show another variation on deploying the curved microwave antenna about a tissue region of interest in which the antenna is partially assembled in situ prior to microwave treatment.
Figure 15D:
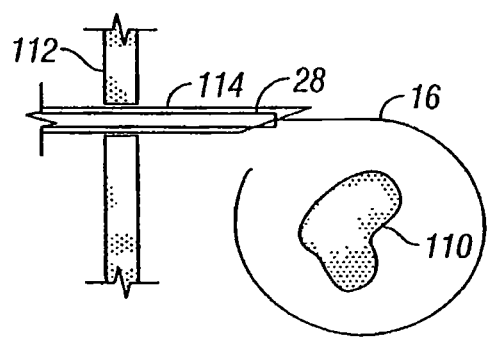

A similar variation may be seen FIGS. 15C and 15D. In this variation, the inner conductor portion with antenna 16 extending therefrom and the surrounding dielectric 28 may be formed without an outer conductor surrounding dielectric 28. Introducer 114 may be used as the outer conductor in constructing the microwave antenna in situ prior to treating the tissue. FIG. 15C shows introducer 114 having been positioned within the tissue adjacent to tumor 110. Antenna 16 and dielectric 28 may be advanced within introducer 114 until dielectric 28 is preferably at the distal end of introducer 114 within the tissue. With antenna 16 surrounding tumor 110 and dielectric 28 properly positioned within introducer 114, ablation of the tissue may be effected with introducer 114 acting as the outer conductor for the microwave antenna.

Figure 15E:
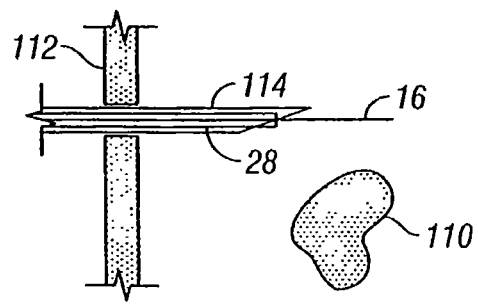
FIGS. 15E and 15F show another variation on deploying the curved microwave antenna about a tissue region of interest where the inner conductor of the antenna is independently advanced through the tissue.
Figure 15F:
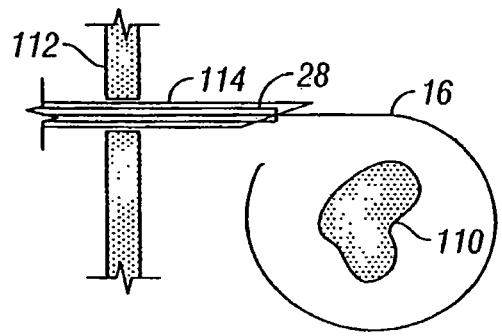

Another alternative is shown in FIGS. 15E and 15F in which introducer 114 and dielectric 28 may be first positioned within the tissue. Once they have been desirably positioned, antenna 16 (inner conductor) may be advanced independently through both dielectric 28 and introducer 114 for placement around tumor 110, as shown in FIG. 15F.

Figure 15G:
FIGS. 15G and 15H show one variation on a method for partially assembling the microwave antenna in situ.
Figure 15H:
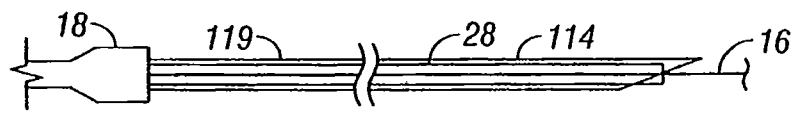

FIGS. 15G and 15H show one variation which allows a microwave antenna to be assembled in situ within the tissue, as described above. Once introducer 114 has been positioned within the tissue, dielectric 28 and antenna 16 may be advanced within introducer 114 from proximal end 119 of introducer 114. Alternatively, they may already be disposed within the introducer 114 during placement within the tissue. In either case, coupler 18 leading to the generator may be electrically connected to antenna 16 at its proximal end and coupler 18 may be advanced distally into mechanical attachment with proximal end 119 such that dielectric 28 and antenna 16 are advanced distally out of introducer 114 and into the tissue. The mechanical attachment between coupler 18 and proximal end 119 may be accomplished by any variety of mechanical fastening methods, e.g., crimping, adhesives, threaded ends, friction fitting, etc. Other examples of antennas which may be assembled in situ are described in further detail in U.S. Pat. Nos. 6,306,132 and 6,355,033 (both to Moorman et al.), each of which is incorporated herein by reference in their entirety. Techniques and apparatus as disclosed in these patents may be utilized in the present invention as examples of assembling the microwave antennas.

Figure 16A:
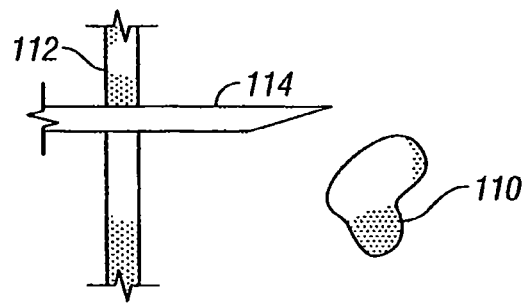
FIGS. 16A to 16D show another variation on deploying the curved microwave antenna about a tissue region of interest in which the introducer may remain in place during antenna deployment.
Figure 16B:
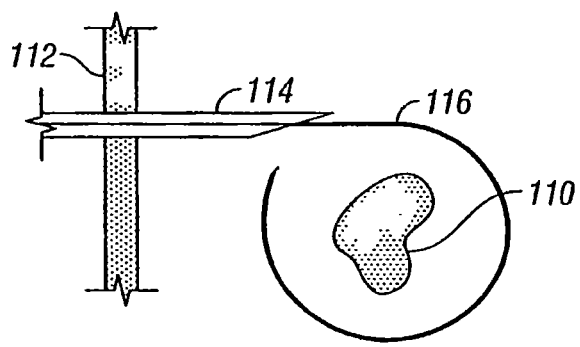
Figure 16C:
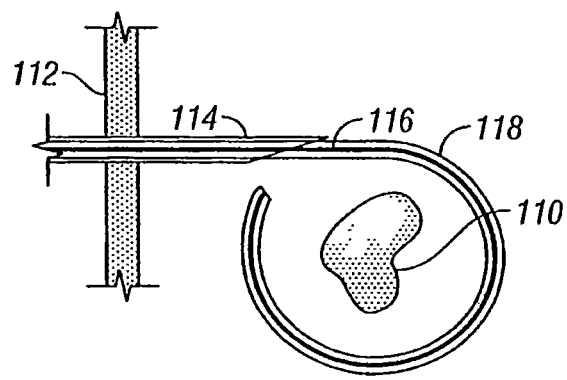
Figure 16D:
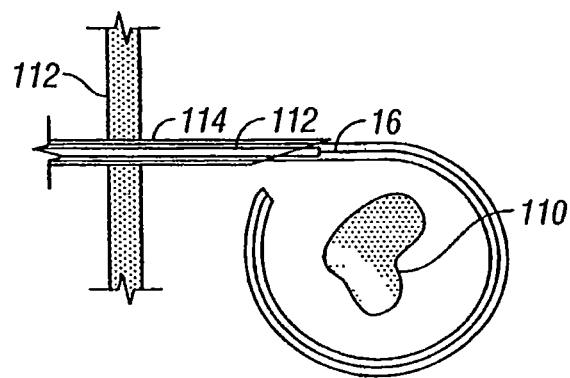

Yet another variation for the deployment is shown in FIGS. 16A to 16D. FIGS. 16A and 16B show the insertion and positioning of introducer 114 and wire 116 adjacent to tumor 110, as described above. However, rather than withdrawing introducer 114 from the tissue, it may be maintained in position while tube 118 is advanced over wire 116 to provide strength to tube 118 as it is advanced over wire 116 through the tissue, as seen in FIG. 16C. FIG. 16D shows wire 116 having been withdrawn from tube 118 and microwave antenna 12 having been advanced through tube 118 while introducer 114 is maintained in position. The operation of microwave antenna 12 may subsequently be accomplished with or without the presence of introducer 114.

Figure 17A:
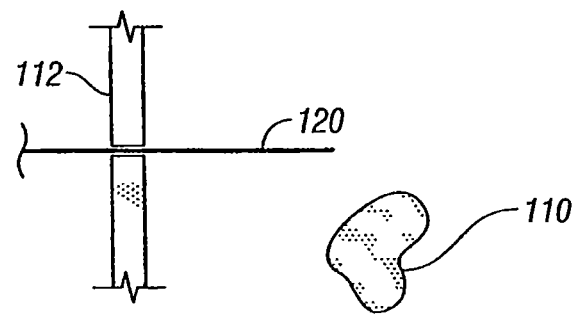
FIGS. 17A to 17D show another variation on deploying the curved microwave antenna using a backstop guide along which the antenna may be guided.
Figure 17B:
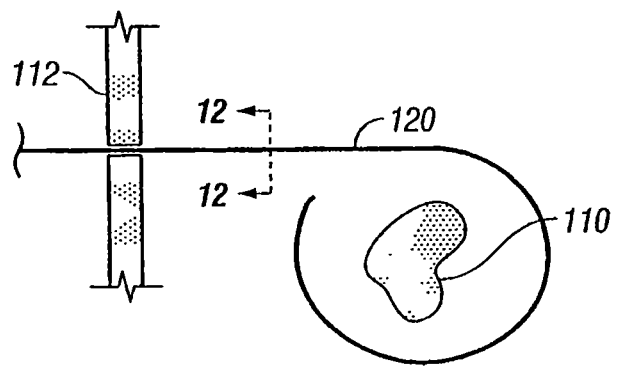
Figure 17C:
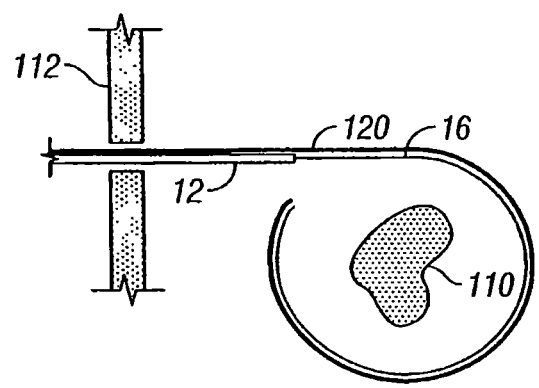
Figure 17D:
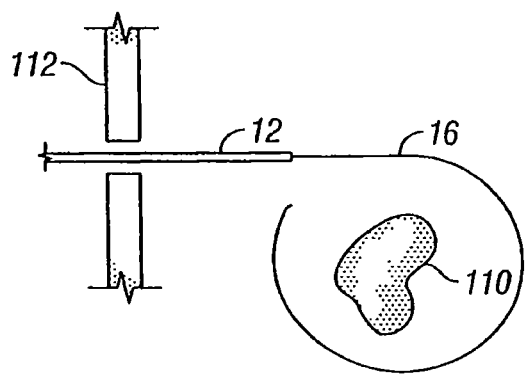
Figure 18A:
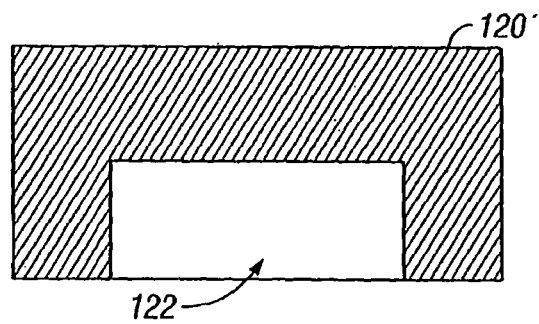
FIGS. 18A and 18B show cross-sectioned variations on the backstop of FIGS. 17A to 17D.
Figure 18B:
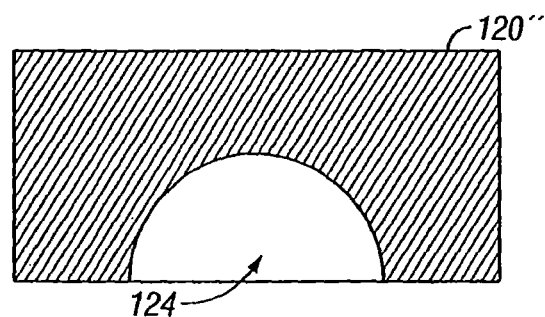

Another variation on the deployment of the microwave antenna is shown in FIGS. 17A to 17D. In this variation, a backstop guide 120 may be utilized rather than a wire 116 or tube 118. Backstop guide 120 is a guide which is preferably configured to define a channel along the length of the backstop 120 within which a microwave antenna 12 may be advanced through or along for positioning antenna 16 about tumor 110. Backstop 120 is preferably made from a shape memory alloy, e.g., Nitinol, which is preconfigured to assume a looped or curved shape for positioning itself about a region of tissue. Variations on the cross-section of backstop guide 120 are shown in FIGS. 18A and 18B. FIG. 17A shows backstop 120 being advanced through skin 112 adjacent to tumor 110. As backstop 120 is further advanced, it preferably reconfigures itself to surround the tissue region to be ablated, e.g., tumor 110, as seen in FIG. 17B. Once backstop 120 has been desirably positioned, microwave antenna 12 may be advanced along backstop 120 as antenna 16 follows the curve defined by backstop 120 around tumor 110, as seen in FIG. 17C. Finally, once microwave antenna 12 has been positioned, backstop 120 may be withdrawn from the tissue area, as seen in FIG. 17D, so that treatment may be effected.

FIGS. 18A and 18B show cross-section variations of backstop 120. FIG. 18A shows one variation where backstop 120' has a channel 122 which has a rectangular configuration and FIG. 18B shows another variation in which backstop 120" has a channel 124 having a rounded channel. When the microwave antenna 12 is deployed using the backstop 120, antenna 16 is preferably guided during deployment through the tissue by traversing within or along channels 122 or 124. Although only two variations on the backstop cross-section are shown, other shapes for the backstop and channel may be utilized and is not intended to be limiting.

A microwave antenna may be deployed either using an introducer and tube, as described above, or it may be inserted directly into the tissue to surround or enclose the tissue region of interest. In either case, during deployment the antenna may encounter resistance from some areas of tissue, particularly in some tissue found, e.g., in the breast. When the microwave antenna encounters resistance, the antenna may simply be pushed through by applying additional force; however, there could be a potential for buckling of the antenna and unnecessary tissue damage. Thus, RF energy may also be utilized with the microwave antenna for facilitating deployment within the tissue. One variation comprises applying RF energy at the distal tip of the antenna as a cutting mechanism during antenna deployment. The microwave antenna is preferably insulated along most of its length, but the distal tip may be uninsulated such that the RF energy may be applied thereto. To utilize the RF energy cutting mechanism at the distal tip, the antenna may be made from Nitinol or other metal. Alternatively, if the tubular antenna variation 100 from FIG. 12C is utilized, a metallic wire may be routed through antenna lumen 102 to the distal tip so that the wire may be used as the RF cutting tip. This wire would be connected to a generator which may supply both the RF and microwave energy. The metallic wire may be made of, e.g., Tungsten or some other appropriate conductive material.

Figure 19A:
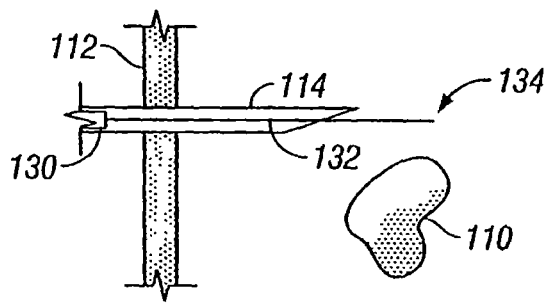
FIGS. 19A to 19D show a variation on the microwave antenna which has an optional RF energy cutting tip.
Figure 19B:
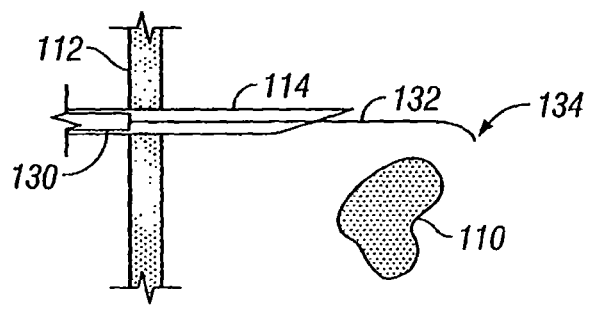
Figure 19C:
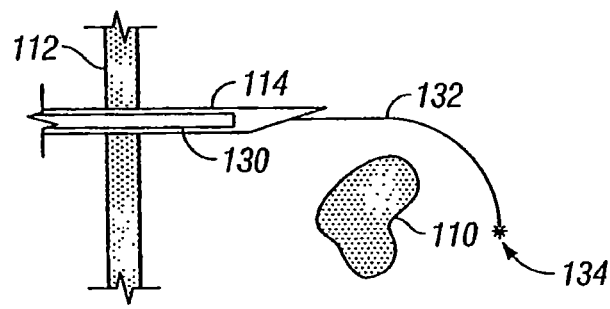
Figure 19D:
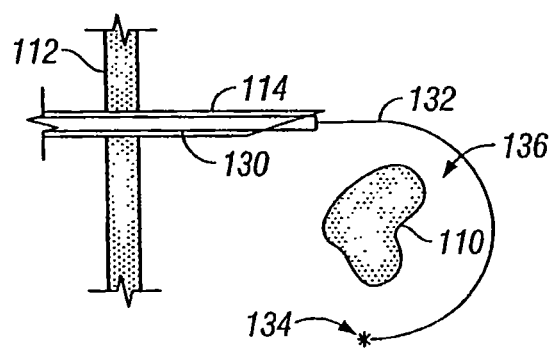

An example of using the RF cutting tip is shown in FIGS. 19A to 19D. After introducer 114 has been positioned adjacent to tumor 110, feedline 130 and antenna 132 may be advanced therethrough. Cutting tip 134 may simply be pushed forward through tissue so long as no resistance is encountered, as shown in FIGS. 19A and 19B. Once resistance from the tissue is encountered, RF energy may be supplied to antenna 132 to activate cutting tip 134, as seen in FIG. 19C. With the RF energy on, antenna 132 may be further advanced, as seen in FIG. 19D, while cutting tip 134 cuts through the obstructive tissue. The RF energy may simply be left on the entire time antenna 132 is advanced through the tissue, or it may be applied or turned on only as needed as cutting tip 134 encounters resistance from the tissue. Once antenna 132 has been desirably positioned about tumor 110, the RF energy, if turned on, may be switched off and the microwave energy may be switched on to effect treatment within the newly created ablation region 136.

Figure 19E:
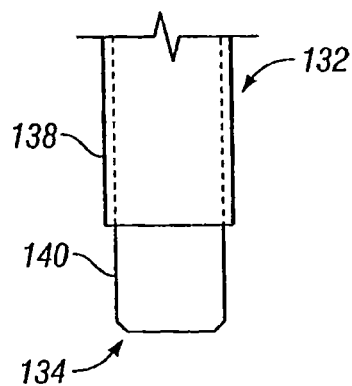
FIG. 19E shows a detailed view of one variation on the RF energy cutting tip.

FIG. 19E shows a detailed view of one variation of cutting tip 134. As shown, antenna 132 may comprise an inner conductor which is preferably covered by insulation 138. To effect the cutting mechanism, distal tip portion 140 may be exposed such that when RF energy is supplied to antenna 132, the exposed tip portion 140 may be utilized to heat and cut through the tissue directly encountered by tip portion 140. The distal tip portion may optionally be tapered or appropriately shaped, such as in a trocar configuration, to further enhance the cutting tip.

Figure 20A:
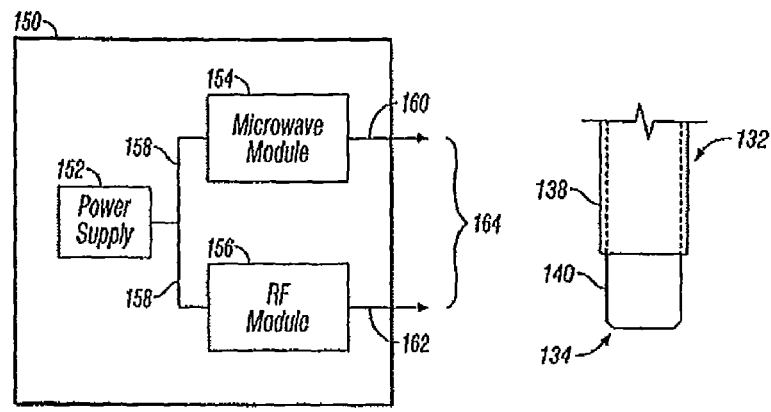
FIGS. 20A and 20B show schematic details of variations of combined microwave and RF energy generators which may be used with the device of FIGS. 19A to 19E.

Given the small amount of surface area of tip portion 140, a low power RF generator may be utilized and can be built into an integral unit along with the microwave generator. Alternatively, the optional RF generator may be physically separated from the microwave generator and may be electrically connected as a separate unit. FIG. 20A schematically shows a variation on generator unit 150 which combines microwave generator module 154 with RF generator module 156 into a single unit 150. Both modules 154, 156 may be supplied by a single power supply 152 also contained within unit 150. Power supply lines 158 may electrically connect the modules 154, 156 to power supply 152. A separate line 160 (e.g., cable) may connect microwave module 154 to microwave antenna 132 and another line 162 may connect RF module 156 to cutting tip 134. Alternatively, the separate lines 160, 162 may be connected into a single line 164 which is electrically connected to both antenna 132 and cutting tip 134 to alternately supply the power for both the microwave and RF energy through the singular connection.

Figure 20B:
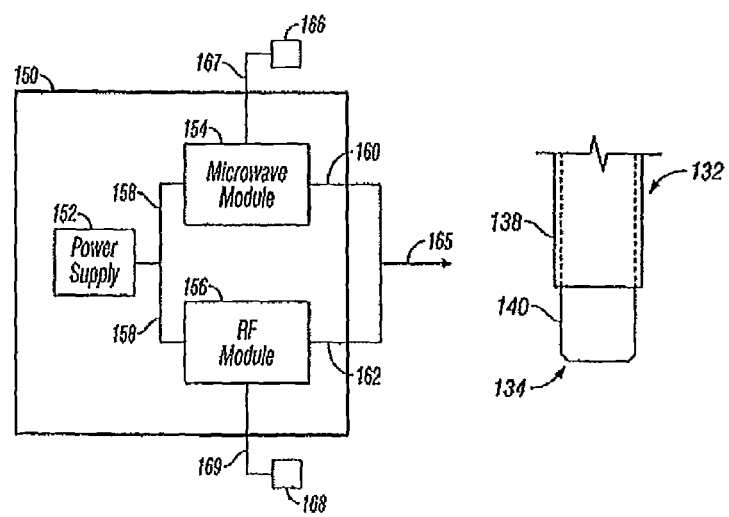

FIG. 20B shows another variation on generator unit 150 in which separate lines 160, 162 are connected into a single output 165, which may be connected to antenna 132 and cutting tip. 134. Also shown are optional switches 166 and 168, which may be connected to microwave and RF modules 154, 156 via lines 167, 169, respectively. Switches 166, 168 may be optionally utilized to enable the surgeon or physician to select the desired output from either or both modules 154, 156 at any time. Switches 166, 168 may accordingly be separate switches or combined into a single unit located remotely from generator unit 150. Furthermore, they may be made in one variation as hand-operated switches or in another variation as foot-operated switches or any variety of actuation switches as may be known in the art.

In addition to utilizing integrally combined RF and microwave generators, another variation which may be utilized involves creating multiple channels from a single unit by multiplexing and cycling the output. This is particularly useful when using multiple microwave antennas, as shown in FIGS. 3 and 4, since the effects of multiple channel generators, which typically requires the use of multiple generators, are accomplished by using a single generator and results in a much lower power consumption. For instance, a three channel 100 W generator system would require about three times the power, i.e., 300 W, as used by a single channel system if the power were produced for each channel simultaneously.

Figure 21:
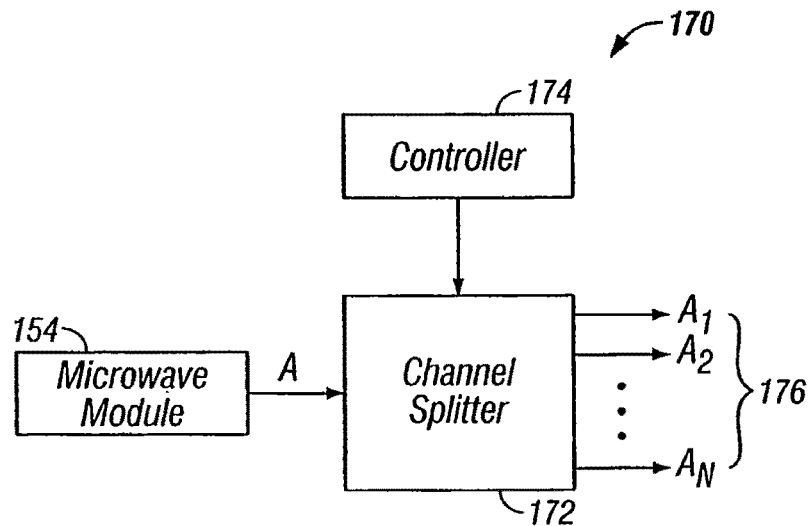
FIG. 21 shows a schematic detail of a channel splitter assembly which may be used to create multiple channels by using a single source.

Accordingly, FIG. 21 schematically shows channel splitter assembly 170 which may be used to create multiple channels by using a single source with multiplexing. A single microwave generator module 154 having, e.g., a 100 W output, may create a single channel "A." The single channel "A" may be switched between several separate channel outputs $A_1$ to $A_N$ created by channel splitter 172. Any number of multiple outputs may be used depending upon the desired number of channels and the desired effects. In use, the output may be cycled through the range of outputs 176 through multiple channels $A_1$ to $A_N$ or in any other manner depending upon the lesion to be created. Moreover, the rate of cycling may range anywhere from several microseconds to several seconds over a treatment period of several minutes or longer.

Controller 174, which is preferably in electrical communication with channel splitter 172 may be used for several purposes. It may be used to control the cycling rate as well as the order of channels in which the output is cycled through. Moreover, controller 174 may be an automatic system or set by the technician or physician. An automatic system may be configured to detect the electrical connection to the antenna and to control the delivery of the energy to the antenna. The detection may be achieved by either a passive or active component in the system which may monitor reflections from the antenna to determine whether a proper connection is present. A controller set by the technician or physician may be configured to require manual initiation for energy delivery to begin.

Additional features which may be utilized for the microwave antennas may include certain safety features. For instance, a connection mechanism may allow for antenna connection with an outer shell of a conventional or custom connector. It may be configured such that an electrical connection may be achieved upon full deployment of the inner conductor curved antenna such that no electrical connection is maintained during deployment. Such a feature could allow an operator to safely assemble and deploy the device without premature microwave antenna activation.

Figure 22:
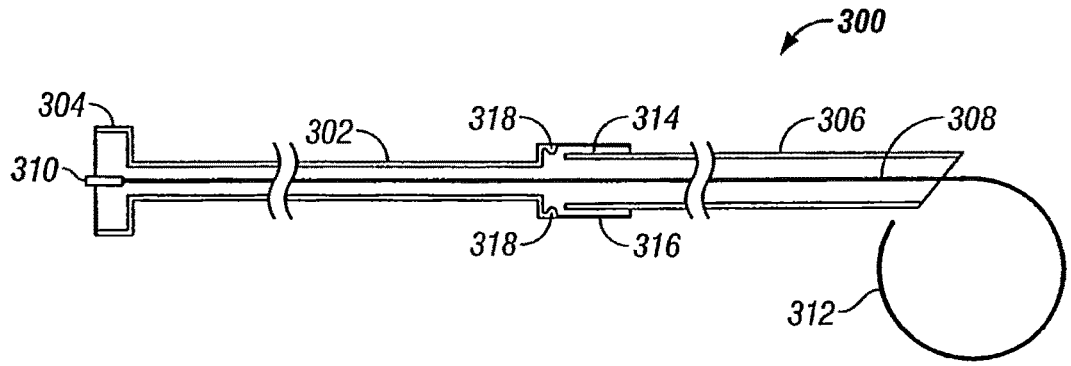
FIG. 22 shows a cross-sectional view of one variation for connecting the microwave antenna assembly.

FIG. 22 shows a cross-sectional view of one variation for connecting microwave antenna assembly 300. In this variation, connector shell 302 may extend from connector 304 and attach to a proximal end of feedline 306. Inner conductor 308 may extend throughout the length of the assembly 300 from pin 310, which may connect to a cable leading to a microwave power generator, and end in curved antenna 312 for deployment within the tissue. The connector shell may contain a feedline, as shown in FIG. 22. To advance curved antenna 312 from within feedline 306 into tissue, receiving connector end 316 of connector shell 302 may be advanced into contact with proximal end 314 of feedline 306. As connector end 316 comes into physical contact with proximal end 314, curved antenna 312 may be advanced out of feedline 306 and into the tissue. Also, retaining member 318, which may simply be a protrusion or other fastener as known in the art, may provide a secure contact between connector shell 302 and feedline 306. Furthermore, retaining member 318 may be an electrically conductive contact such that it also provides a secure electrical communication path between connector shell 302 and feedline 306 to allow for the microwave energy to be transmitted between the two. This feature may also act as a safety feature in that curved antenna 312 is preferably fully deployed out of feedline 306 before the electrical connection is made between feedline 306 and connector shell 302.

Figure 23:
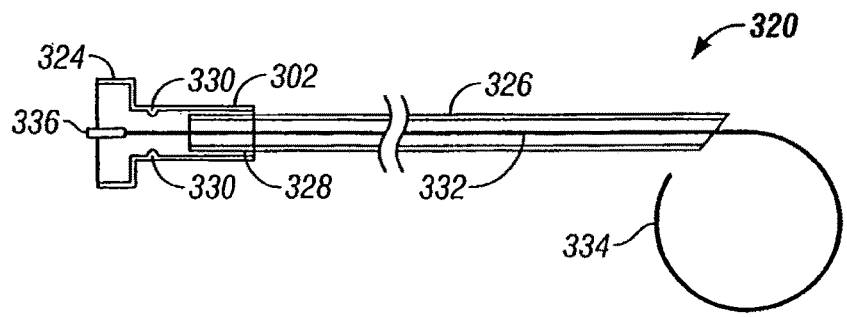
FIG. 23 shows a cross-sectional view of another variation for connecting the microwave antenna assembly.

FIG. 23 shows a cross-sectional view of another variation for connecting microwave antenna assembly 320. This variation 320 shows connector shell 322 which may be shortened from the previous variation 300. As shown, proximal end 328 of feedline 326 may receivingly extend into connector shell 322 and into contact with retaining member 330, which may be configured similarly as above. Inner conductor 332 may extend through assembly 320 from pin 336 within connector 324 to curved antenna 334. As feedline 326 is placed into secure electrical contact with connector shell 322 via retaining member 330, curved antenna 324 may be advanced distally out of feedline 326.

Figure 24A:
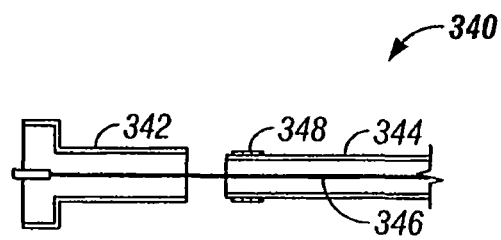
FIGS. 24A to 24C show alternative variations for connecting the microwave antenna assembly using protrusions located on the feedline.
Figure 24B:
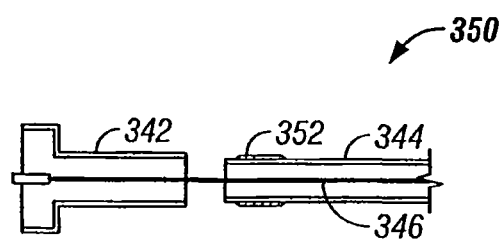
Figure 24C:
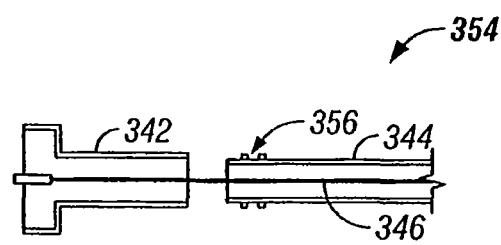

In addition to or in place of the retaining members described above, protrusions may instead-be placed on-an outer surface of the antenna feedline. As shown in FIG. 24A, one variation may be seen in antenna assembly 340. Connector 342 may be seen prior to connection with a proximal end of feedline 344. Inner conductor 346 is shown extending through connector 342 and feedline 344, while plating layer 348 may be seen upon an outer surface of feedline 344. Layer 348 may be made from a conductive material, e.g., solder, or other conductive metal. FIG. 24B shows another variation in antenna assembly 350 which has a layer of plating 352 having tapered edges to facilitate insertion of feedline 344 within connector 342. FIG. 24C shows yet another variation in antenna assembly 354 in which multiple separate layers 356 of plating may be utilized. These variations are merely illustrative and any number of other various configurations may be utilized depending upon the desired results.

Figure 25A:
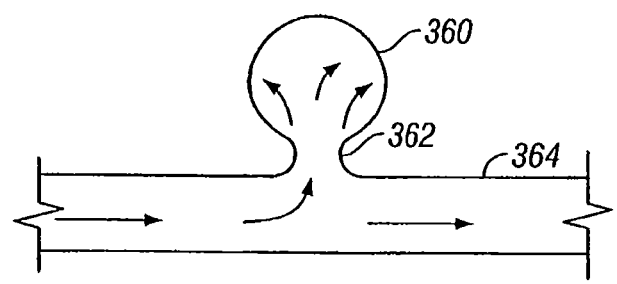
FIGS. 25A and 25B show an example of another possible application for the microwave antenna in sealing aneurysms.
Figure 25B:
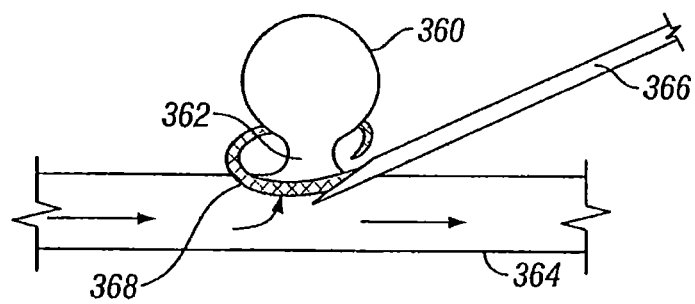

Any of the antenna variations and methods for use and deployment described herein may be utilized in a variety of medical treatments aside from tumor ablation. For example, a curved microwave antenna be used to seal an aneurysm 360 extending from a body vessel 364, as seen in FIG. 25A. In such use, the surgeon or physician may inject a contrast agent into the patient's circulatory system. Then, with the assistance of an X-ray imager, e.g., a fluoroscope, the surgeon may locate the aneurysm 360. Introducer 366 of the antenna device may be inserted into the tissue and the tip of introducer 366 may be placed adjacent to neck 362 of aneurysm 360. Curved antenna 368 may be deployed around neck 362 of aneurysm 360, as seen in FIG. 25B. Microwave energy may be directed through curved antenna 368 to ablate neck 362 located within the ablation region. Curved antenna 368 may then be retracted back into introducer 366 and the device may be then withdrawn from the subject's body.

Figure 26A:
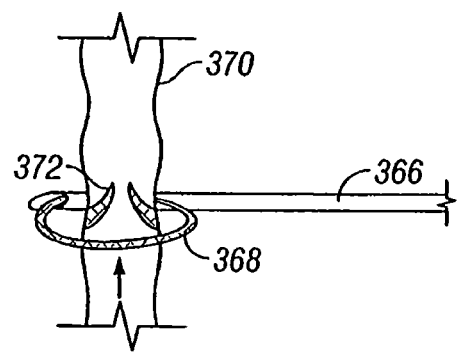
FIGS. 26A and 26B show another example of a possible application in coagulating malfunctioning valves in a vessel.
Figure 26B:
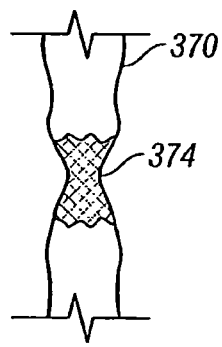

In another example of application, curved antenna 368 may be utilized to occlude vessel 370 as shown in FIG. 26A. As shown, curved antenna 368 may be deployed around the tissue of interest, in this case vessel 370 instead of the neck of an aneurysm. The vessel 370 in this example has a malfunctioning valve 372. Microwave energy may be directed through curved antenna 368 and into vessel 370, which is positioned within the ablation region of antenna 368, to induce a coagulated region 374 of blood to halt the flow of blood in the vessel 370, as shown in FIG. 26B.

Figure 27A:
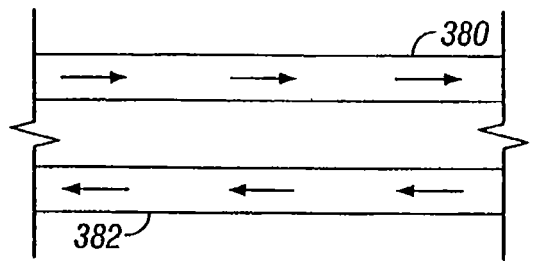
FIGS. 27A to 27D show another example of a possible application in coagulating fistulas formed between adjacent vessels.
Figure 27B:
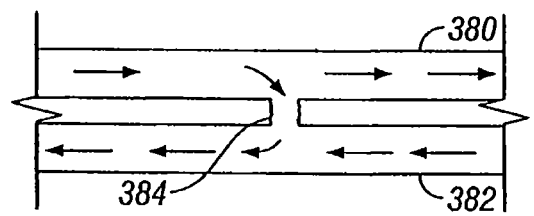
Figure 27C:
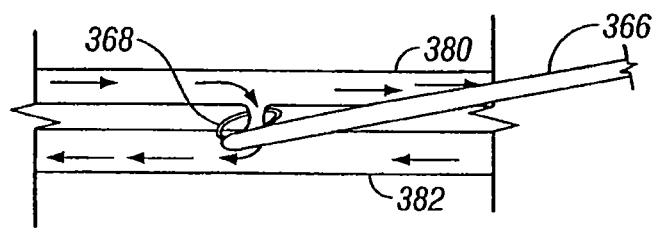
Figure 27D:
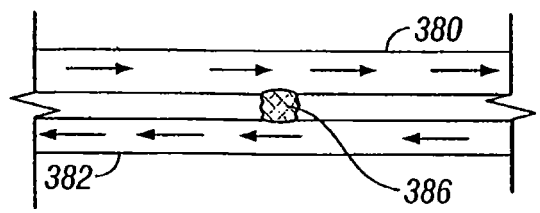

In yet another example, the microwave antenna may be used to treat a fistula. As shown in FIG. 27A, in a normal condition, e.g., an artery 380 and, e.g., a vein 382, are located adjacent to each other and typically have blood flow that is isolated from each other. An abnormality known as a fistula 384 may permit the passage of blood flow from, e.g., an artery 380 to a vein 382, as shown in FIG. 27B. Curved microwave antenna 368 may be used to seal the fistula 384 between the two blood vessels 380, 382 using methods similarly described above, as shown in FIG. 27C. Once the energy has been applied, the fistula 384 may form coagulated region 386 and seal fistula 384, as shown in FIG. 27D.

In addition to sealing hollow body organs, any of the antenna variations described herein may additionally be used for the ablation of bone metastases, e.g., osteoid osteomas, osteoblastomas, spinal metastases, etc. Due to the ablation region created by the curved microwave antenna, using the antenna is a viable option for treating such conditions or for alleviating pain. To effect microwave energy treatment in regions within bone, the curved antenna may be inserted through a biopsy needle using any of the methods described above.

Figure 28A:
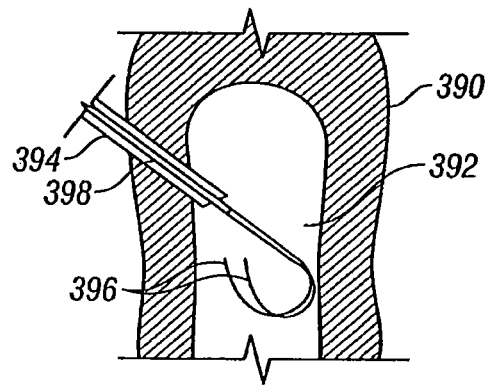
FIGS. 28A and 28B show another example of a possible application in treating the soft core of a bone.
Figure 28B:
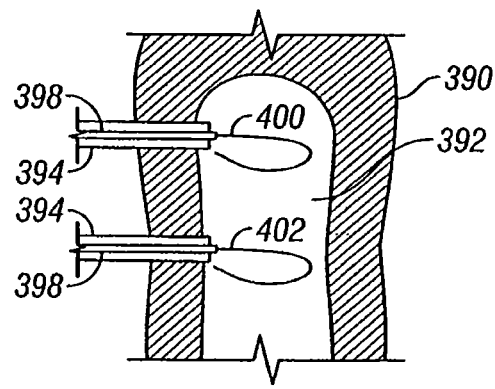

As shown in one example in FIG. 28A, introducer 394 may be inserted within bone 390 through cortical bone and into, e.g., the medullary cavity 392. Once the distal end of introducer 394 has accessed cavity 392, feedline 398 and curved antenna 396 may be inserted through introducer 394 and deployed within cavity 392. This example illustrates antenna 396 as having multiple curved antennas; however, a single curved antenna or a plurality of curved antennas may be used depending upon the desired results. Once antennas 396 have been deployed within cavity 392, the antennas may be used to ablate regions of the soft core of bone 390, e.g., to de-nerve the region for pain reduction, or to kill cancerous cells, etc. FIG. 28B shows another example in which a number of separate curved antennas 400, 402 may be introduced into cavity 392 to ablate the region. Antennas 400, 402 may be introduced and positioned adjacently to one another in a parallel configuration, as shown or described above or using any number of guide assemblies described above, or at various angles relative to one another. Although only two antennas are shown in the FIG. 28B, any number of antennas may be utilized as practicable. Any number of antenna configurations may also be utilized, as described above, as practicable depending upon the desired ablation results.

The applications of the microwave antenna and methods of use discussed above are not limited to regions of the body but may include any number of further treatment applications. Other treatment sites may include areas or regions of the body such as other organ bodies. Moreover, various other antenna shapes and partial shapes may be utilized beyond what is described herein. Modification of the above-described assemblies and methods for carrying out the invention, and variations of aspects of the invention that are obvious to those of skill in the art are intended to be within the scope of the claims.

What is claimed is:

1. A system for delivering electrosurgical energy, comprising:
    an electrosurgical energy generator including a RF energy source and a microwave energy source;
    a microwave antenna having a distal portion configured to electrosurgically cut tissue, the microwave antenna configured to couple to the electrosurgical energy generator;
    a first line configured to electrically connect the RF energy source to the distal portion of the microwave antenna for electrosurgically cutting tissue; and
    a second line configured to electrically connect the microwave energy source to the microwave antenna, wherein the electrosurgical energy source is configured to simultaneously deliver microwave energy and RF energy to the microwave antenna.

2. The system according to claim 1, further comprising a power supply coupled to the microwave energy source and the RF energy source, the power supply configured to power each of the microwave energy source and the RF energy source.

3. The system according to claim 1, further comprising a switch operably coupled to the electrosurgical energy generator and configured to switch between delivery of microwave energy and RF energy.

4. The system according to claim 1, wherein the electrosurgical energy generator includes a first output coupled to the RF energy source and a second output coupled to the microwave energy source, the first line coupled to the first output and the second line coupled to the second output.

5. The system according to claim 1, wherein the electrosurgical energy generator includes an output coupled to both the RF energy source and the microwave energy source, the first line and the second line coupled to the output.

6. The system according to claim 1, further comprising:
    a first switch operably coupled to the RF energy source and configured to control output of the RF energy source; and
    a second switch operably coupled to the microwave energy source and configured to control output of the microwave energy source.

7. A system for delivering electrosurgical energy, comprising:
    an electrosurgical energy generator including a RF energy source and a microwave energy source;
    a microwave antenna configured to couple to the electrosurgical energy generator and having a portion configured to electrosurgically cut tissue;
    a first line configured to electrically connect the RF energy source to the portion of the microwave antenna for electrosurgically cutting tissue; and
    a second line configured to electrically connect the microwave energy source to the microwave antenna, wherein the electrosurgical energy source is configured to simultaneously deliver microwave energy and RF energy to the microwave antenna.

8. The system according to claim 7, further comprising a power supply coupled to the microwave energy source and the RF energy source, the power supply configured to power each of the microwave energy source and the RF energy source.

9. The system according to claim 7, further comprising a switch operably coupled to the electrosurgical energy generator and configured to switch between delivery of microwave energy and RF energy.

10. The system according to claim 7, wherein the electrosurgical energy generator includes a first output coupled to the RF energy source and a second output coupled to the microwave energy source, the first line coupled to the first output and the second line coupled to the second output.

11. The system according to claim 7, wherein the electrosurgical energy generator includes an output coupled to both the RF energy source and the microwave energy source, the first line and the second line coupled to the output.

12. The system according to claim 7, further comprising:
- a first switch operably coupled to the RF energy source and configured to control output of the RF energy source; and
- a second switch operably coupled to the microwave energy source and configured to control output of the microwave energy source.

* * * * *